US011464182B2

(12) United States Patent
Muramoto et al.

(10) Patent No.: US 11,464,182 B2
(45) Date of Patent: Oct. 11, 2022

(54) METHOD OF INDUCING GENETIC RECOMBINATION, AND USE THEREFOR

(71) Applicants: KABUSHIKI KAISHA TOYOTA CHUO KENKYUSHO, Nagakute (JP); TOYOTA JIDOSHA KABUSHIKI KAISHA, Toyota (JP)

(72) Inventors: Nobuhiko Muramoto, Nagakute (JP); Hidenori Tanaka, Nagakute (JP); Hiroki Sugimoto, Nagakute (JP); Norihiro Mitsukawa, Nagakute (JP); Akinori Ikeuchi, Nagakute (JP); Risa Nakamura, Nagakute (JP); Ritsuko Yogo, Nagakute (JP); Satoshi Katahira, Nagakute (JP); Chikara Ohto, Toyota (JP); Satoshi Kondo, Miyoshi (JP)

(73) Assignees: KABUSHIKI KAISHA TOYOTA CHUO KENKYUSHO, Nagakute (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 15/740,312

(22) PCT Filed: Jul. 1, 2016

(86) PCT No.: PCT/JP2016/069721
§ 371 (c)(1),
(2) Date: Dec. 27, 2017

(87) PCT Pub. No.: WO2017/002977
PCT Pub. Date: Jan. 5, 2017

(65) Prior Publication Data
US 2018/0184606 A1    Jul. 5, 2018

(30) Foreign Application Priority Data

Jul. 2, 2015 (JP) .............................. JP2015-133902
Dec. 2, 2015 (JP) .............................. JP2015-236072

(51) Int. Cl.
*C12N 15/00* (2006.01)
*A01H 1/08* (2006.01)
*A01H 1/04* (2006.01)
*C12N 15/10* (2006.01)
*C12N 15/82* (2006.01)
*A01H 1/06* (2006.01)
*C12N 9/22* (2006.01)

(52) U.S. Cl.
CPC ................ *A01H 1/08* (2013.01); *A01H 1/04* (2013.01); *A01H 1/06* (2013.01); *C12N 15/102* (2013.01); *C12N 15/827* (2013.01); *C12N 15/8213* (2013.01); *C12N 15/8241* (2013.01); *C12N 15/8261* (2013.01); *C12N 9/22* (2013.01); *Y02A 40/146* (2018.01)

(58) Field of Classification Search
CPC ... A01H 1/04; A01H 1/06; A01H 1/08; C12N 15/8241; C12N 9/22; C12N 15/102; C12N 15/8213; C12N 15/8261; C12N 15/827; Y02A 40/146
See application file for complete search history.

(56) References Cited

U.S. PATENT DOCUMENTS

| 4,697,546 A * | 10/1987 | Chrisman ............... A01K 67/02 119/217 |
| 7,638,680 B2 | 12/2009 | Carman |
| 8,258,369 B2 | 9/2012 | Wakamatsu |
| 8,268,620 B2 | 9/2012 | Thomson et al. |
| 8,889,412 B2 | 11/2014 | Lim et al. |
| 2003/0005479 A1* | 1/2003 | Kato ........................ A01H 1/08 800/260 |
| 2008/0166809 A1 | 7/2008 | Ohta et al. |
| 2010/0184227 A1 | 7/2010 | Thomson et al. |
| 2011/0277189 A1 | 11/2011 | Kondo et al. |
| 2013/0102479 A1 | 4/2013 | Lim et al. |
| 2013/0217117 A1 | 8/2013 | Thomson et al. |
| 2014/0273126 A1* | 9/2014 | Muramoto ..... C12Y 301/21004 435/160 |

FOREIGN PATENT DOCUMENTS

| JP | H04-108359 A | 4/1992 |
| JP | H11-151050 A | 6/1999 |
| JP | 2002-510964 A | 4/2002 |
| JP | 2006-141322 A | 6/2006 |
| JP | 1169213 B2 | 10/2008 |
| JP | 2011-160798 A | 8/2011 |

(Continued)

OTHER PUBLICATIONS

Soriano et al., Effects of colchicine on anther and microspore culture of bread wheat (*Triticum aestivum* L.); Plant Cell Tiss Organ Cult, vol. 91, pp. 225-234, 2007 (Year: 2007).*
Pomper et al., Genetic analysis of polyploidy yeast; Genetics, vol. 39, No. 343, 1953 (Year: 1953).*
Ikeda et al., Two attempts upon improving an industrial strain of aspergillus oryzae through somatic recombination and polyploidization; J Gen. Appl. Microbiol. Voll. 3, No. 2, 1957 (Year: 1957).*
Chopra, V.L., Mutagenesis: Investigating the process and processing the outcome for crop improvement; Current Science, vol. 89, No. 2, 2005 (Year: 2005).*
Song et al in "Polyploid Organisms", Sci China Life Sci, 2012, vol. 55: pp. 301-311. (Year: 2012).*
Hantzschel & Weber (Protoplasma 2010, vol. 241, pp. 99-104). (Year: 2010).*

(Continued)

*Primary Examiner* — Catherine S Hibbert
(74) *Attorney, Agent, or Firm* — Oliff PLC

(57) ABSTRACT

A method of inducing genetic recombination, including: allowing a protein having DNA double-stranded cleavage activity to act in cells of a eukaryotic organism which is a polyploidy inherently possessed by a eukaryotic organism. In eukaryotic organisms, various genetic recombination generates new genome set composition. This is done to obtain a population of eukaryotic organisms that hold the modified genomic set.

19 Claims, 21 Drawing Sheets

(56) References Cited

FOREIGN PATENT DOCUMENTS

| | | |
|---|---|---|
| JP | 2012-044883 A | 3/2012 |
| JP | 2012-506702 A | 3/2012 |
| JP | 2013-511274 A | 4/2013 |
| JP | 2014-171466 A | 9/2014 |
| JP | 2015-073480 A | 4/2015 |
| NO | 98/33374 A1 | 8/1998 |
| WO | 2010/048567 A1 | 4/2010 |
| WO | 2011/062559 A1 | 5/2011 |

OTHER PUBLICATIONS

Grosser et al in "Protoplast fusion for production of tetrapioids and triploids: applications for scion and rootstock breeding in citrus" (Plant Cell Tiss Organ Cult 2011, vol. 104: pp. 343-357). (Year: 2011).*

Soriano et al in "Effects of colchicine on anther and microspore culture of bread wheat *Triticum aestivum*" (Plant Cell Tiss Organ Cult, vol. 91, pp. 225-234, 2007. (Year: 2007).*

Ikeda et al in "Two attempts upon improving an industrial strain of Aspergillus oryzae through somatic recombination and polyploidization" (J Gen. Appl. Microbiol. Voll. 3, No. 2, 1957; of record). (Year: 1957).*

Ekino et al in "Engineering of Polyploid *Saccharomyces cerevisiae* for Secretion of Large Amounts of Fungal Glucoamylase" (Applied and Environmental Microbiology, Nov. 2002 vol. 68, No. 11, pp. 5693-5697). (Year: 2002).*

Storchová et al. "Genome-wide genetic analysis of polyploidy in yeast." Nature, Oct. 2006, vol. 443, pp. 541-547.

Pavelka et al. "Aneuploidy confers quantitative proteome changes and phenotypic variation in budding yeast." Nature, Nov. 2010, vol. 468, pp. 321-325.

Hartung et al. "The Catalytically Active Tyrosine Residues of Both SPO11-1 and SPO11-2 are Required for Meiotic Double-Strand Break Induction in *Arabidopsis*" The Plant Cell, Oct. 2007, vol. 19, pp. 3090-3099.

Tsukaya. "Controlling Size in Multicellular Organs: Focus on the Leaf." PLoS Biology, Jul. 2008, vol. 6, pp. 1373-1376.

Tang et al. "Gene Copy-Number Alterations: A Cost-Benefit Analysis." Cell, Jan. 2013, vol. 152, pp. 394-405.

Oct. 4, 2016 Written Opinion issued in International Application No. PCT/JP2016/069721.

Oct. 4, 2016 International Search Report issued in International Patent Application No. PCT/JP2016/069721.

Keuchi et al. "A novel breeding method; genome rearrangement induced by multiple DNA double strand breaks in *Saccharomyces cerevisiae*." BMB2015 Online Yoshi, Nov. 2015.

Tanaka et al. "De novo mutations induced by multiple DNA double strand breaks are revealed by whole-genome sequencing of *Arabidopsis thaliana*." BMB2015 Online Yoshi, Nov. 2015.

Oct. 10, 2017 Office Action issued in Japanese Patent Application No. 2015-236072.

May 8, 2018 Office Action issued in Japanese Patent Application No. 2015-236072.

Senovilla, L., et al. "An Immunosurveillance Mechanism Controls Cancer Cell Ploidy." Science, vol. 337, 2012, pp. 1678-1684.

D'Amato, F. "Polyploidy in Cell Differentiation." Caryologia, vol. 42, No. 3-4,1989, pp. 183-211.

Barrett, T. B., et al. "Polyploid nuclei in human artery wall smooth muscle cells." Proceedings of National Academy of Science USA vol. 80,1983, pp. 882-885.

Shi, Q., et al. "Chromosome nondisjunction yields tetrapioid rather than aneuploid cells in human cell lines." Nature. vol. 437, 2005, pp. 1038-1042.

Harris, M. "Polyploid Series of Mammalian Cells." Experimental Cell Research. vol. 66, 1971, pp. 329-336.

Horii, T., et al. "p53 Suppresses Tetrapioid Development in Mice." Scientific Reports. vol. 5:8907, 2015, pp. 1-9.

Yokoyama, T., et al. "Induction of hexaipoid by hot water treatment of inseminated eggs in the silkworm, *Bombyx mori*" Journal of Sericultural Science of Japan. vol. 65, No. 3, 1996, pp. 151-156.

McCombie, H., et al. "A Complementary Method for Production of Tetrapioid Crassostrea gigas Using Crosses Between Diploids and Tetrapioids with Cytochalasin B Treatments." Marine BioTechnology, vol. 7, 2005, pp. 318-330.

Song, C., et al. "Polyploid organisms." Science China, vol. 55, No. 4, 2012, pp. 301-311.

Wertheim, B., et al. "Polyploidy in Animals: Effects of Gene Expression on Sex Determination, Evolution and Ecology." Cytogenetic and Genome Research, vol. 140, 2013, pp. 256-269.

Schmid, M., et al. "Polyploidy in Amphibia." Cytogenetic and Genome Research, vol. 145, 2015, pp. 315-330.

Piferrer, F., et al. "Polyploid fish and shellfish: Production, biology and applications to aquaculture for performance improvement and genetic containment." Aquaculture, vol. 293, No. 3-4, 2009, pp. 125-156.

Kawamura, N. "Male Meiosis in Polyploid Silkworms, *Bombyx mori* L. (Lepidoptera: Bombycidae)." Journal of Insect Morphology and Embryology, vol. 23, No. 4,1994, pp. 311-317.

Storchova, Z., et al. "The consequences of tetraploidy and aneuploidy." Journal of Cell Science, vol. 121, 2008, pp. 3859-3866.

\* cited by examiner

MORPHOLOGICAL CHANGES TETRAPLOID CONTROL STRAIN AND TETRAPLOID TaqI-INTRODUCED PLANTS

COPY NUMBER ANALYSIS BY TILING ARRAY OF CHROMOSOMES OF MORPHOLOGICALLY ALTERED STRAINS OF TETRAPLOID TaqI-INTRODUCED PLANTS
Relative level DETERMINED BY FORMULA (Relative level = $\mathrm{Log}_{10}(\mathrm{Cy5}_{SAMPLE}/\mathrm{Cy3}_{Col-0})$),
AND AVERAGE VALUES OF 20 CONTINUOUS PROBES OF CHROMOSOME SHOWN.

PLOIDY HISTOGRAMS OF DIPLOID AND TETRAPLOID WILD STRAINS AND DIPLOID AND TETRAPLOID TaqI-INTRODUCED LINES

DRY WEIGHT INCREASE IN PROGENY OF OCTAPLOID TaqI-INTRODUCED LINES

GROWTH OF OCTAPLOID WILD STRAIN AND TaqI-INTRODUCED OCTAPLOID LINE 40 DAYS AFTER SOWING

COPY NUMBER ANALYSIS BY TILING ARRAY OF TCL878_P8-5#3 CHROMOSOME
Relative level DETERMINED BY FORMULA (Relative level = $\text{Log}_{10}(\text{Cy5}_{TCL878\_P8-5\#3}/\text{Cy3}_{Col-0})$),
AND AVERAGE VALUES OF 20 CONTINUOUS PROBES OF CHROMOSOME SHOWN.

ESTIMATED COPY NUMBERS FOR EACH CHROMOSOME WERE
chr1: 6 COPIES, chr2: 6 COPIES, chr3: 6 COPIES (REARRANGED REGION 1: 8 COPIES),
chr4: 5 COPIES, chr5: 7 COPIES COMPARISON OF TaqI EXPRESSION
USING BY4741+GFP(HIS) STRAIN AT VARIOUS INDUCTION TEMPERATURES GENOME REARRANGEMENT EFFICIENCY DUE TO TRANSIENT HEAT TREATMENT
USING BY4741+GFP(HIS) STRAIN

A. IMMEDIATELY AFTER HEAT TREATMENT, B. AFTER RECOVERY CULTURE

GENOME REARRANGEMENT EFFICIENCY DUE TO MILD HEAT TREATMENT
USING BY4741+GFP(HIS) STRAIN

COMPARISON OF GENOME REARRANGEMENT EFFICIENCY
USING HAPLOID, DIPLOID AND TETRAPLOID YEASTS

PLOIDY HISTOGRAMS BY TaqI TREATMENT TIME
USING HAPLOID, DIPLOID AND TETRAPLOID YEASTS

METHOD OF INDUCING GENETIC RECOMBINATION, AND USE THEREFOR

CROSS-REFERENCE TO RELATED APPLICATIONS

Technical Field

This application is a related application to Japanese Patent Application No. 2015-133902 filed on Jul. 2, 2015 and Japanese Patent Application No. 2015-236072 filed on Dec. 2, 2015, and claims priority based on these applications, the entire contents of which are hereby incorporated by reference into the present Description.

The present Description relates to a method for inducing genetic recombination, a use therefor, and the like.

Background

Increasing the mass of biological resources (biomass), and plant biomass in particular, is considered effective not only for increasing food production, but also for conserving the global environment, preventing global warming and reducing production of greenhouse gasses. Consequently, the creation of useful plants and techniques for increasing plant biomass is extremely important.

Microorganisms are also used effectively in a variety of industries. For example, yeasts having various properties such as high temperature tolerance, high alcohol tolerance, and high alcohol synthesis ability have the potential to provide lower-cost ethanol fermentation in the field of bioethanol production using polysaccharides such as cellulose as raw materials.

In general, the properties of useful plants and microorganisms are quantitative traits that are influenced by expression of multiple genes rather than a single gene. To modify a quantitative trait by normal mutation treatment, the treatment must span a vast number of generations because the trait changes obtained with a single operation are small.

Methods are therefore being developed whereby large-scale genome rearrangement can be achieved efficiently in order to modify quantitative traits (Patent Literature 1, 2, 3). It has been reported that with these methods, a mutant population with a variety of genome configurations can be obtained by causing a so-called restriction enzyme to be expressed transiently in cells to thereby induce DNA breakage in the genome as a whole and achieve multiple simultaneous genome rearrangements.

Chromosome doubling is also highly significant for improving plant varieties and the like. In the case of wheat for example, hexaploid common wheat has been cultivated from diploid single-grain wheat. It is thought that such genome doubling has helped to provide agriculturally useful properties such as improved productivity and threshability. The creation of resistant plants by artificial induction of genome doubling (Patent Literature 4) and the creation of yeasts with improved stress resistance by artificial induction of chromosome aneuploidy (Non Patent Literature 1) have been reported.

In plants, however, a condition called "high ploidy syndrome" has been reported, in which increased ploidy has a negative effect on plant growth (Non Patent Literature 2). Moreover, chromosome aneuploidy, in which the ploidy of only a specific chromosome is increased, has been reported to cause various genetic diseases in animals, and to reduce fertility and induce abnormal growth in plants (Non Patent Literature 3). Moreover, a tetraploid-specific lethal gene has also been reported in a yeast of an application (Non Patent Literature 4). In yeasts, moreover, continuous culture of 1,000 or more generations is required to select a yeast with a desirable trait (Non Patent Literature 5).

SUMMARY

Technical Problem

Various techniques have been attempted for rearranging the genome to obtain organisms with useful traits. However, although various kinds of genome rearrangement provide useful traits, they also have negative effects such as deleting desirable traits or inserting undesirable traits. Consequently even using these methods it is extremely difficult and time-consuming to select organisms having useful quantitative traits.

To obtain an organism having a superior quantitative trait, it is essential to create an even more diverse population of the organism, and then apply selection to this population. When constructing an organism population with even greater diversity, it is also necessary to suppress lethal expression and the like and prevent favorable traits from being lost or degraded. However, no effective method has yet been developed for achieving such diverse genetic recombination.

In view of the above, the present Description provides a method for inducing genetic recombination, and a use therefor.

Solution to Problem

The inventors focused on a combination of chromosome doubling and double-stranded DNA breakage treatment as a means of creating a eukaryote population with even greater diversity. It was then discovered that diverse genetic recombination could be achieved by causing a protein having double-stranded DNA breakage ability to act within the cells of a parent eukaryote of which chromosomes have been basically doubled. That is, a way was discovered of rapidly creating a highly diverse population of a eukaryote. The present Description provides the following means based on these findings.

(1) A method of inducing genetic recombination in a eukaryote, comprising modifying a genome set by allowing a protein having double-stranded DNA breakage activity to act within cells of a eukaryote that is a polyploid having a ploidy greater than the inherent ploidy of the eukaryote.

(2) The method according to (1), wherein the genetic recombination is one or two or more selected from the group consisting of genetic mutation by substitution, insertion or deletion of one or two or more bases, chromosome inversion, unequal crossover, crossover, translocation, duplication and deletion, copy number decrease, copy number increase, chromosome polyploidization and chromosome aneuploidization.

(3) The induction method according to (1) or (2), wherein the eukaryote is a polyploid having tetraploid or higher ploidy.

(4) The induction method according to any of (1) to (3), wherein the genetic recombination includes chromosome aneuploidization.

(5) The induction method according to any of (1) to (4), wherein the genetic recombination includes a genome size decrease or increase.

(6) The induction method according to any of (1) to (5), wherein the genetic recombination includes deletion or duplication of part of a chromosome.

(7) The induction method according to any of (1) to (6), wherein the modifying artificially activates the double-stranded DNA breakage activity of the protein.

(8) The induction method according to any of (1) to (7), wherein the modifying applies a temperature lower than the optimum temperature for the double-stranded DNA breakage activity of the protein.

(9) The induction method according to any of (1) to (8), wherein modifying uses the protein, obtained by expressing an exogenous gene coding for the protein.

(10) The induction method according to any of (1) to (9), wherein the protein is a frequent restriction enzyme.

(11) The induction method according to (10), wherein the frequent restriction enzyme is a restriction enzyme derived from a thermophilic bacterium.

(12) The induction method according to (11), wherein the frequent restriction enzyme is TaqI.

(13) The induction method according to any of (1) to (12), wherein the eukaryote is a plant.

(14) The induction method according to any of (1) to (13), wherein the eukaryote is a microorganism.

(15) The induction method according to any of (1) to (14), further comprising polyploidizing in which a parent eukaryote is obtained artificially by a genome size increase operation before the modifying.

(16) The induction method according to (15), wherein the polyploidizing uses a doubling inducing agent.

(17) The induction method according to (14), wherein the polyploidizing uses cell fusion.

(18) A method of producing a modified eukaryote, comprising modifying a genome set by allowing a protein having double-stranded DNA breakage activity to act within cells of a eukaryote that is a polyploid having a ploidy greater than the inherent ploidy of the eukaryote.

(19) The production method according to (18), further comprising selecting a target eukaryote based on any indicator.

(20) A method of producing a population of a eukaryote, comprising modifying a genome set by allowing a protein having double-stranded DNA breakage activity to act within cells of a eukaryote that is a polyploid having a ploidy greater than the inherent ploidy of the eukaryote. such that a eukaryote population carrying a modified genome set is obtained.

(21) A breeding material that is a eukaryote having a ploidy greater than the inherent ploidy, and expressably carries a gene coding for a protein having double-stranded DNA breakage ability.

(22) A method of producing a breeding material, comprising:
applying an artificial genome size increase operation one or two or more times to a eukaryote that is a polyploid having a ploidy greater than the inherent ploidy to thereby obtain a eukaryote of the desired ploidy; and
transforming the eukaryote with the desired ploidy in such a way that a gene coding for a protein having double-stranded DNA breakage activity can be expressed.

(23) A method of producing a breeding material, comprising:
transforming a eukaryote that is a polyploid having a ploidy greater than the inherent ploidy in such a way that a gene coding for a protein having double-stranded DNA breakage activity can be expressed; and
applying an artificial genome size increase operation one or two or more times to the transformed eukaryote to thereby obtain a transformed eukaryote of the desired ploidy.

DESCRIPTION OF EMBODIMENTS

Figure 1:
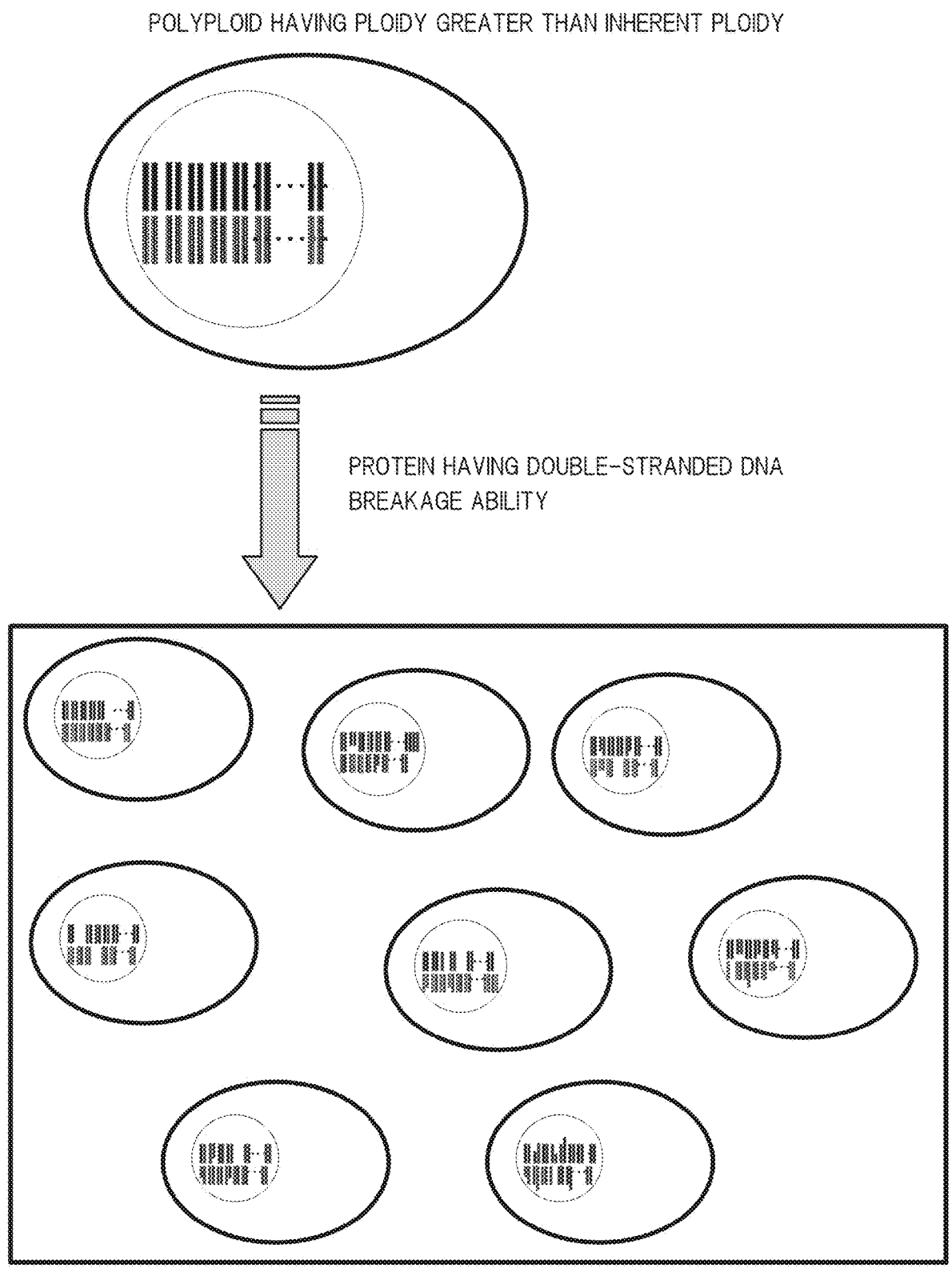
FIG. 1 gives a summary of this disclosure.

This disclosure of the present Description relates to a method for inducing genetic recombination, and to a use therefor. FIG. 1 shows an outline of this method for inducing genetic recombination disclosed in the present Description. As shown in FIG. 1, in this induction method the genome set of a eukaryote is modified by causing a protein having double-stranded DNA breakage activity to act within the cells of a eukaryotic organism that is a polyploid having a ploidy greater than the inherent ploidy of the eukaryote (called the inherent ploidy in the present Description). The polyploidized genome set of the eukaryote encompasses various genetic recombinations that result when implementing cut at various sites with a double-stranded DNA breakage enzyme.

Because each of the individual eukaryotes carries a genome set resulting from a different genetic recombination, it is possible to construct a eukaryote population with a highly diverse genome set composition. The resulting eukaryote population with a highly diverse genome set composition is at the same time a eukaryote population with a highly diverse morphology.

Because this induction method uses a eukaryote that is a polyploid having a ploidy greater than the inherent ploidy, lethal individuals are less likely to occur due to large-scale chromosome deletion. Moreover, the increased number of chromosomes means that chromosomal aneuploidy is more likely, and large-scale genome rearrangement can also be induced more frequently. The genome sets produced by such genetic recombination may encompass various mutations in addition to large changes such as chromosomal aneuploidy and deletion regions. Consequently, this production method can yield a population consisting of individual eukaryotes having various morphologies.

Conventionally, mutant breeding with mutagenic agents, gamma rays and the like is considered difficult in tetraploids and higher polyploids and the like having a ploidy greater than the inherent ploidy because genes are duplicated and latent mutations are likely to be concealed. However, by causing a protein having double-stranded DNA breakage activity to act within the cells of such a polyploid, it is possible to suppress the conventional drawbacks and exploit the advantages of the polyploid to thereby achieve diverse genetic recombinations and obtain a eukaryote population having a diversity of genome set compositions and morphologies. A method for producing such a diverse eukaryote population becomes a useful tool for promoting breeding of eukaryotes.

Because functional damage to genes and chromosomes due to genetic recombination in genome sets carried by eukaryotes can be suppressed with this induction method, it is possible to ensure a diversity of genome set compositions by genetic recombination. As a result, it is possible to efficiently exploit the advantages of chromosome doubling while simultaneously avoiding problems associated with chromosome doubling (genome size increase) in eukaryotes. It is thus possible to construct a eukaryote population that is also diverse in terms of morphology.

It is thought that this eukaryote population is a population of eukaryotes in which morphologies may have been acquired, improved, lost, reduced, modified or the like in various ways, such as eukaryotes that have acquired new morphologies that may occur in the course of evolution, those in which morphologies have been lost, and those in which morphologies have been degraded or improved.

Consequently, a target eukaryote can be efficiently obtained by subjecting a eukaryote population obtained by the method of this disclosure to selection based on a desired indicator.

In the present Description, a "genome set" is DNA that is present as chromosomal DNA in a eukaryotic cell, is self-replicable in eukaryotic cells, and is transmitted to daughter cells.

In the present Description, "genetic recombination" is used in a broad sense to mean the phenomena of DNA cleavage and recombination occurring between DNAs. Consequently, "genetic recombination" in the present Description encompasses homologous recombination and heterologous recombination. Moreover, "genetic recombination" in the present Description also encompasses genetic mutations involving substitution, insertion, deletion and the like of one or two or more bases, and chromosomal mutations such as chromosome inversion, unequal crossover, crossover, translocation, duplication and deletion, copy number decrease, copy number increase, chromosome polyploidization and chromosome aneuploidization.

"Ploidy" in general means the number of genome sets possessed by an organism. The term "(poly)ploid" in general is a way of designating an organism according to the number of genome sets it possesses, such as haploid, diploid or triploid.

In the present Description, the "inherent ploidy of a eukaryotic organism" means the number of genome sets inherently possessed by a eukaryotic organism, each consisting of a number of chromosomes (basic number) corresponding to one genome set in the eukaryotic organism. This is also called "inherent ploidy" in the present Description.

More specifically, "inherent ploidy" may be the number of genome sets that is believed to be possessed inherently by members of the same species or a related species of eukaryote. For example, animals are generally diploid, so their inherent ploidy is diploidy. Plants have a variety of inherent ploidies. In microorganisms for example, yeasts may be haploid or diploid, but from the standpoint of the life cycle the inherent ploidy is diploid.

In the present Description, a "polyploid having a ploidy greater than the inherent ploidy" means that the eukaryotic organism has a number of genome sets in excess of the inherent ploidy.

In animals, a "polyploid having a ploidy greater than the inherent ploidy" may mean a polyploid greater than diploid. In plants, various polyploids are possible. A "polyploid having a ploidy greater than the inherent ploidy" may be a homologous polyploid, or a heterogenous polyploid derived from hybridization or the like. Moreover, a "polyploid having a ploidy greater than the inherent ploidy" may be an integral multiple polyploid, or an aneuploid having aneuploidy in which the number of some chromosomes is mutated. The ploidy of the chromosomes of a eukaryote can be determined by conventional known methods, or with a flow cytometer or tiling array as shown in examples below.

Typical and non-limiting embodiments of this disclosure are explained below with reference to the appropriate drawings. These detailed explanations are simply meant to provide a person skilled in the art with the details for implementing preferred examples of the disclosure, and are not meant to limit the scope of this disclosure. Additional features and inventions disclosed below may be used either separately or together with other features and disclosures to provide a further improved method for inducing genetic recombination and use therefor.

Furthermore, the combinations of features and steps disclosed in the detailed explanations below are not necessary for implementing this disclosures in the broadest sense, and are only described for purposes of explaining typical examples of this disclosure in particular. The various features of the typical examples given above and below and the various features described in the independent and dependent claims need not be combined as in the specific examples described here or in the order listed when providing additional useful embodiments of this disclosure.

All features described in the present Description and/or Claims are meant to be disclosed separately and independently from one another as limitations on the specific matter claimed and this disclosure of the original application, separately from the configurations of features described in the examples and/or Claims. Moreover, all descriptions of numerical ranges and groups or populations are meant to include intermediate configurations as limitations on the specific matter claimed and this disclosure of the original application.

(Method for Inducing Genetic Recombination)

The method for inducing genetic recombination of this disclosure (hereunder sometimes called the induction method) may comprise a modification step in which the genome set of a eukaryote is modified by causing a protein having double-stranded DNA breakage activity (hereunder called this protein) to act within the cells of a eukaryote that is a polyploid having a ploidy greater than the inherent ploidy of the eukaryote. Because this induction method includes such a modification step, it allows for various genetic recombinations in individual eukaryotes, with the result that a eukaryote population can be obtained carrying modified genome sets. That is, by causing this protein to act within the cells of a parent eukaryote originally having a genome set of a single composition, it is possible to obtain a population consisting of multiple eukaryotes that are highly diverse in terms of genome set composition and morphology.

(Modification Step)

(Eukaryote)

This induction method can be applied to any eukaryotic organism. Examples of eukaryotic organisms to which this induction method is applicable include animals, plants and eukaryotic microorganisms. The animals are not particularly limited, and examples include mammals and various non-mammals such as fish. The animal to which this induction method is applied may also be anything derived from an animal, and may be in the form of a cell, tissue, organ or fertilized egg. For purposes of obtaining a modified animal, it is convenient if it is in a form such as a fertilized egg having the ability to regenerate into a complete animal.

The plant to which this induction method is applied is also not particularly limited, and examples include dicotyledonous plants and monocotyledonous plants, such as those belonging to the Brassicaceae, Gramineae, Solanaceae, Leguminosae and Salicaceae (see below).

Brassicaceae: *Arabidopsis thaliana, Brassica rapa, Brassica napus,* cabbage (*Brassica oleracea* var. capitata), Napa cabbage (*Brassica rapa* var. pekinensis), *Brassica rapa* var. chinensis, turnip (*Brassica rapa* var. rapa), *Brassica rapa* var. hakabura, *Brassica rapa* var. lancinifolia, *Brassica rapa* var. peruviridis, Chinese cabbage (*Brassica rapa* var. chinensis), daikon (*Brassica Raphanus* sativus), wasabi (*Wasabia japonica*), etc.

Solanaceae: Tobacco (*Nicotiana tabacum*), eggplant (*Solanum melongena*), potato (*Solaneum tuberosum*), tomato (*Lycopersicon lycopersicum*), pepper (*Capsicum annuum*), petunia, etc.

Leguminosae: Soy beans (*Glycine max*), peas (*Pisum sativum*), fava beans (*Vicia faba*), wisteria (*Wisteria floribunda*), peanuts (*Arachis hypogaea*), bird's foot trefoil (*Lotus corniculatus* var. japonicus), garden beans (*Phaseolus vulgaris*), azuki beans (*Vigna angularis*), Acacia, etc.

Asteraceae: Chrysanthemum (*Chrysanthemum morifolium*), sunflower (*Helianthus annuus*), etc.

Arecaceae: Oil palm (*Elaeis guineensis, Elaeis oleifera*), coconut palm (*Cocos nucifera*), date palm (*Phoenix dactylifera*), carnauba palm (*Copernicia*), etc.

Anacardiaceae: Japanese wax tree (*Rhus succedanea*), cashew (*Anacardium occidentale*), lacquer tree (*Toxicodendron vernicifluum*), mango (*Mangifera indica*), pistachio (*Pistacia vera*), etc.

Cucurbitaceae: Squash (*Cucurbita maxima, Cucurbita moschata, Cucurbita pepo*), cucumber (*Cucumis sativus*), snake gourd (*Trichosanthes cucumeroides*), bottle gourd (*Lagenaria siceraria* var. gourda), etc.

Rosaceae: Almond (*Amygdalus communis*), rose (*Rosa*), strawberry (*Fragaria*), cherry (Prunus), apple (*Malus pumila* var. domestica), etc.

Caryophyllaceae: Carnation (*Dianthus caryophyllus*), etc.

Salicaceae: Poplar (*Populus trichocarpa, Populus nigra, Populus tremula*), etc.

Gramineae: Corn (*Zea mays*), rice (*Oryza sativa*), barley (*Hordeum vulgare*), wheat (*Triticum aestivum*), bamboo (*Phyllostachys*), sugar cane (*Saccharum officinarum*), napier grass (*Pennisetum pupureum*), *Erianthus ravenae, Miscanthus virgatum, sorghum,* switch grass (*Panicum*), etc.

Liliaceae: Tulip (*Tulipa*), lily (*Lilium*), etc.

Myrtaceae: *Eucalyptus* (*Eucalyptus camaldulensis, Eucalyptus grandis*), etc.

The plant to which this induction method is applied may also be anything derived from a plant, and for purposes of obtaining a modified plant, it is convenient if it is in a form having the ability to regenerate into a complete plant. Thus, the plant may be in the form of a cell, tissue, organ, seed, callus or the like.

The microorganisms are also not particularly limited, but from the standpoint of material production and the like, examples include molds such as koji mold and other microbial cells such as yeasts. Examples of molds include *Aspergillus* species such as *Aspergillus aculeatus* and *Aspergillus orizae.* In terms of yeasts, various kinds of known yeasts may be used, but examples include *Saccharomyces* yeasts such as *Saccharomyces cerevisiae, Schizosaccharomyces* yeasts such as *Schizosaccharomyces pombe, Candida* yeasts such as *Candida shehatae, Pichia* yeasts such as *Pichia stipitis, Hansenula* yeasts, *Klocckera* yeasts, *Schwanniomyces* yeasts, *Yarrowia* yeasts, *Trichosporon* yeasts, *Brettanomyces* yeasts, *Pachysolen* yeasts, *Yamadazyma* yeasts, *Kluyveromyces* yeasts such as *Kluyveromyces marxianus* and *Kluyveromyces lactis,* and *Issatchenkia* yeasts such as *Issatchenkia orientalis.* Of these, a *Saccharomyces* yeast is preferred from the standpoint of industrial utility and the like, and *Saccharomyces cerevisiae* is especially desirable.

(Preparation of Eukaryote)

A eukaryote that is a polyploid having a ploidy greater than the inherent ploidy is used in this induction method. The eukaryote having a ploidy greater than the inherent ploidy in which genetic recombination is induced is also called a parent eukaryote. Using such a polyploid as a parent eukaryote allows for a variety of genetic recombinations by double-stranded DNA breakage, and makes it possible to dramatically and efficiently construct a population rich in genome set composition and diversity of morphological traits.

A polyploid having a ploidy greater than the inherent ploidy may be used as the parent eukaryote. In an animal for example, a parent eukaryote having a ploidy greater than diploid may be used as the polyploid having a ploidy greater than the inherent ploidy because the inherent ploidy of animals is diploid. Because plants have a variety of inherent ploidies, a parent eukaryote having a ploidy greater than the inherent ploidy in that case may be used. For microorganisms, a parent eukaryote having a ploidy greater than diploid may be used in the case of yeasts and the like.

The polyploid having a ploidy greater than the inherent ploidy may be of a wild type. For example, wheat exists in a diploid wild form but in a case where there exist also wild-type wheats with ploidies exceeding diploid, such as tetraploid and hexaploid wheat, and such tetraploid and higher wheat may also be used. A eukaryote obtained artificially by a genome size increase operation may also be used as the parent eukaryote.

The parent eukaryote is preferably a tetraploid or higher polyploid. Examples of tetraploid or higher polyploids include tetraploids as well as pentaploids, hexaploids, septaploids and octaploids. With this disclosure, the problems associated with large genome size can be avoided and a diverse eukaryote population that exploits the advantages of genome size can be obtained by genetic recombination of a genome set through double-stranded DNA breakage even if the chromosome ploidy is high. Consequently, if the inherent ploidy of the parent eukaryote is tetraploid or higher, the genetic recombination efficiency is increased, and an especially diverse eukaryote population can be constructed. Pentaploidy is more preferred, hexaploidy is still more preferred, septaploidy is even more preferred and octaploidy or higher is still even more preferred.

The parent eukaryote may also be a parent eukaryote that has been made to exceed its inherent ploidy by an artificial genome size increase operation. When using such a parent eukaryote, a parent eukaryote that has been obtained ahead of time or an existing parent eukaryote that was obtained by an artificial genome size increase operation may also be subjected to the modification step. Alternatively, a step may be performed of subjecting a eukaryote to a genome size increase operation to obtain a parent eukaryote stably having a ploidy greater than the inherent ploidy, and the modification step may then be performed on the parent eukaryote obtained in this step.

Examples of artificial genome size increase operations include cell fusion using various kinds of cells, suppression of meiosis by heat or pressure in fertilized or unfertilized eggs of animals, plant hybridization, and supplying a chromosome doubling inducing agent such as colchicine. In the case of yeasts, examples include selection and separation of low frequency zygotes between common heterotrimer strains, and methods involving mating type switching systems and cell fusion (Biochemical Experimental Methods Volume 39, Experiments in Yeast Molecular Genetics (Yasuharu Oshima, Gakkai Shuppan Center)). A person skilled in the art can apply known techniques to a suitable eukaryote to obtain a parent eukaryote having a ploidy greater than the inherent ploidy.

(Protein: Protein Having Double-Stranded DNA Breakage Activity)

In this step, this protein, i.e., a protein having double-stranded DNA breakage ability, is made to act within the cells of a parent eukaryotic organism. this protein is not particularly limited, but typically a known double-stranded DNA breakage enzyme may be used. Because large-scale genome rearrangement using a parent eukaryote with a ploidy greater than the inherent ploidy is allowed in this induction method, the influence of the characteristics of the double-stranded DNA breakage activity (recognition site (i.e. frequency), etc.) of this protein is avoided or suppressed, so a known double-stranded DNA breakage enzyme can be appropriately selected and used.

The breakage site (recognition site) of the double-stranded DNA breakage enzyme is not particularly limited. From the standpoint of genetic recombination efficiency, the double-stranded DNA breakage enzyme is preferably a so-called frequent restriction enzyme having a roughly 4-base to 6-base recognition site on the DNA. Because the number of breakage sites in the genome is a factor in genome rearrangement efficiency, chromosomal DNA can be broken with the desired frequency by providing a recognition site with this number of bases. For example, a double-stranded DNA breakage enzyme having a 4-base or 5-base recognition site is more desirable and one having a 4-base recognition site is still more desirable. Examples of such double-stranded DNA breakage enzymes are not particularly limited but include ApeKI, BsrI, BssKI, BstNI, BstUI, BtsCI, FatI, FauI, PhoI, PspGI, SmlI, TaqI, TfuI, TseI, Tsp45I and TspRI. Other examples include various known frequent enzymes such as Sse9I, MseI, DpnI and CviAII.

More preferably, the restriction enzyme is derived from a thermophilic bacterium, and has an optimum temperature for double-stranded DNA breakage activity in a temperature range higher than the culture temperature of the cells of the parent eukaryote. This means that this protein can be activated and its activity reduced by temperature treatment at any time, which is convenient for the temporary action of this protein. Moreover, the activity of such a protein can be regulated by means of temperature. Furthermore, relatively mild double-stranded DNA breakage activity can be achieved with such a protein. For example, a restriction enzyme with an optimum temperature of 50° C. to 80° C. for double-stranded DNA breakage activity can be used as such a protein. For example, the optimum temperature may be 50° C., 55° C., 60° C., 65° C. or 75° C. (catalog values in all cases). The optimum temperature of a restriction enzyme may be selected based on the catalogs of various commercial companies (catalog values) or the like. If the optimum temperature is less than 50° C., the double-stranded DNA breakage activity may be too strong. If the optimum temperature exceeds 80° C., the double-stranded DNA breakage activity may be too weak. In general, the optimum temperature is preferably at least 55° C., or more preferably at least 60° C., or may be at least 62° C. or about 65° C. Moreover, in general the optimum temperature is preferably not more than 75° C., or more preferably not more than 70° C., or may be not more than 68° C.

For example, the following known restriction enzymes may be appropriately selected and used as this protein.

TABLE 1

| Optimun temperature ° C. | Restriction enzyme |
| --- | --- |
| 50 | ApoI |
|  | BclI |
|  | BfuAI |
|  | BspQI |
|  | BSSHI |
|  | BtsCI |
|  | Nt.BspQI |
|  | SfiI |
| 55 | BsiWI |
|  | BslI |
|  | BsmAI |
|  | BsmBI |
|  | BtsI |

TABLE 1-continued

| Optimun temperature ° C. | Restriction enzyme |
|---|---|
|  | FatI |
|  | FauI |
|  | Nt.BstNBI |
|  | SmlI |
|  | Sse9I |
| 60 | BsaBI |
|  | BsaJI |
|  | BsaWI |
|  | BsiEI |
|  | BssKI |
|  | BstAPI |
|  | BstEII |
|  | BstNI |
|  | BstUI |
|  | BstYI |
|  | BtgZI |
|  | MwoI |
| 65 | BsiHKAI |
|  | BsmFI |
|  | BsmI |
|  | BsrDI |
|  | BsrI |
|  | BstBI |
|  | Nb.BsmI |
|  | Nb.BsrDI |
|  | PI-PspI |
|  | TaqI |
|  | TfiI |
|  | TseI |
|  | Tsp45I |
|  | Tsp509I |
|  | TspRI |
|  | Tth111I |
|  | AccIII |
| 75 | ApeKI |
|  | PhoI |
|  | PspGI |
|  | TspMI |

In terms of recognition sites and the like, ApeKI, BsrI, BssKI, BstNI, BstUI, BtsCI, FatI, FauI, PhoI, PspGI, SmlI, Sse9I, TaqI, TfuI, TseI, Tsp45I and TspRI are suitable restriction enzymes for use as this protein. From the standpoint of optimum temperature and the like, examples include ApeKI, BsaBI, BsaJI, BsaWI, BsIEI, Bs1I, BsmBI, BsmI, BspQI, BsrDI, BsrI, BssKI, BstAPI, BstBI, BstNI, BstUI, BstYI, FatI, FauI, MwoI, Nb.BsmI, Nb.BsrDI, PspGI, SfiI, SmlI, TaqI, TfiI, TliI, TseI, Tsp45I, Tsp509I, TspMI, TspRI and Tth111I.

In order for this protein to act within the cells of the parent eukaryote, this protein must at least be present inside the cells. The protein is inherently present inside the cell, but is preferably supplied from the outside. The protein may be supplied directly to the cells of the parent eukaryote, or else an expression vector capable of expressing a gene coding for this protein may be supplied to the parent eukaryote to transform the eukaryote. Preferably, this protein may be made to act by inducing expression thereof within the cells of the parent eukaryote. The action of this protein can thus be expressed with the desired timing.

A vector that causes this protein to be expressed within the cells of the parent eukaryote can be constructed by a person skilled in the art by conventional known methods using appropriate cell types and transformation techniques. Nucleotide sequences coding for this protein are available from various databases. A vector suited to the cells may also be obtained appropriately, and the desired expression cassette constructed, and a desired expression cassette for which a suitable promoter, terminator or enhancer is selected may be constituted. A nuclear localization signal useful in the eukaryote may also be included, although this is not a limitation.

For example, various conventionally known vectors may be used as hosts of expression vectors for expressing the protein in plant cells. For example, plasmids, phages, cosmids or the like may be used, and may be selected appropriately according to the introduction method and the plant cells into which the vector is to be introduced. Specific examples include pBR322, pBR325, pUC19, pUC119, pBluescript, pBluescriptSK and pBI vectors. A pBI binary vector is especially desirable when the method of introducing the vector into the plant is a method using an *Agrobacterium*. Specific examples of pBI binary vectors include pBIG, pBIN19, pBI101, pBI121 and pBI221.

The promoter is not particularly limited as long as it is a promoter capable of causing expression of a restriction enzyme gene in a plant, and a known promoter may be used appropriately. Examples of this promoter include the cauliflower mosaic virus 35S promoter (CaMV35S), various actin gene promoters, various ubiquitin gene promoters, a nopaline synthase gene promoter, a tobacco PR1a gene promoter, a tomato ribulose 1,5-biphosphate carboxylase/oxidase small subunit gene promoter, and a napin gene promoter. As discussed below, a promoter with an expression intensity lower than that of the 35S promoter, such as a SIG2 promoter derived from an *Arabidopsis thaliana* sigma factor (AtSIG2) for example, is preferred.

The expression vector may also contain another DNA segment in addition to the promoter and the restriction enzyme gene. This other DNA segment is not particularly limited, and may be a terminator, selection marker, enhancer, or nucleotide sequence for increasing translation efficiency or the like. The recombinant expression vector may also have a T-DNA region. The T-DNA region can increase the efficiency of gene introduction when the recombinant expression vector is introduced into a plant using an *Agrobacterium* in particular.

The transcription terminator is not particularly limited as long as it functions as a transcription termination site, and a known terminator may be used. Specifically, a nopaline synthase gene transcription termination region (Nos terminator) or cauliflower mosaic virus 35S transcription termination region (CaMV35S terminator) for example may be used by preference. Of these, a Nos terminator is especially desirable.

In addition, known elements may be selected and used appropriately as the selection marker and nucleotide sequence for increasing translation efficiency. The method for constructing the expression vector is not particularly limited, and the necessary elements may be introduced appropriately into an appropriately selected host vector.

This expression vector is then introduced into plant cells in such a way that the protein is transiently or constantly expressed. To transiently express the protein, for example the expression vector is physically introduced, as a plasmid, into plant cells using the PEG method, electroporation method or particle gun method. In the case of constant expression, it is incorporated into the plant genome by the *Agrobacterium* method or the like.

The *Agrobacterium* method is advantageous for ensuring a diversity of genome sets because it can reduce the rate of plant cell death due to introduction of the gene coding for this protein. The *Agrobacterium* method is preferably applied to dicotyledonous plants, particularly *Arabidopsis thaliana*.

A conventional known method can be used appropriately as a method of regenerating a plant from the transformed plant cells or the like.

To cause expression of this protein within the cells of yeasts or the like, a suitable expression vector for yeasts can be constructed in the same way and introduced into a yeast. A person skilled in the art can construct an expression vector by known methods using a suitable enhancer other than a promoter and a terminator. An expression cassette can be configured for introduction into the chromosome, or may be configured so that it is carried outside the chromosome.

When constructing the expression vector, it is desirable to use an inducible promoter so that the timing of protein expression can be deliberately determined. The other control regions such as the promoter and terminator are also selected appropriately so as to set the desired level of expression intensity.

For example, the inducible promoter may be a glactose-inducible promoter such as GAL1 or GAL10, a promoter used in an induction system such as a Tet-on system/Tet-off system in which induction and removal are achieved by addition of doxycycline, or a promoter for a gene coding for a heat-shock protein (HSP) such as HSP10, HSP60 and HSP90, but it is desirable to use the CUP1 promoter, which is activated by addition of copper ions. Using the CUP1 promoter, cells can be cultured in medium that contains a carbon source such as glucose but no copper ions, after which a copper ion compound can be added to the medium, and the cells cultured to induce expression of the double-stranded DNA breakage enzyme. The added concentration of copper ions can be set appropriately, and may be in the range of about 50 µM to 300 µM for example. The culture time can be about 1 to 6 hours. Moreover, the cells are preferably cultured at a temperature outside the activation conditions of the double-stranded DNA breakage enzyme (for example, 30° C.) so that the double-stranded DNA breakage enzyme is not activated during expression induction. One advantage of the CUP1 promoter is that it allows deliberate expression induction and activation of the double-stranded DNA breakage enzyme to be achieved easily and rapidly.

Based on conventional known methods, a person skilled in the art can introduce such an expression vector into a yeast so that the gene is carried within or outside the chromosome of the transformed yeast.

(Parent Eukaryote Expressably Carrying Gene Coding for this Protein)

A parent eukaryote capable of expressably carrying a gene coding for this protein can be used as the parent eukaryote. In this case, such a gene can be introduced into a candidate parent eukaryote having the desired ploidy to effect transformation and obtain a parent eukaryote having the desired ploidy. This candidate parent eukaryote having the desired ploidy can be obtained by performing an artificial genome increase operation one or two or more times on a eukaryote having a ploidy greater than the inherent ploidy.

Following such gene introduction and transformation of a eukaryote that is a polyploid having a ploidy greater than the inherent ploidy, an artificial genome increase operation can be performed one or two or more times on the transformant to obtain a parent eukaryote having the desired ploidy.

Thus, the parent eukaryote is also a breeding material for preparing a eukaryote or eukaryote population for breeding purposes or the like. Consequently, this disclosure of the present Description also provides a parent eukaryote useful as a breeding material that can be used favorably in this induction method, and an induction method therefor. A breeding material that is a eukaryote having a ploidy greater than the inherent ploidy and expressably carrying a gene coding for a protein having double-stranded DNA breakage activity is provided by this disclosure.

An induction method suited to producing the breeding material of this disclosure may comprise a step of performing an artificial genome increase operation one or two or more times on a eukaryote having an inherent ploidy to thereby obtain a eukaryote having the desired ploidy, and a step of transforming this eukaryote having the desired ploidy in such a way that a gene coding for a protein having double-stranded DNA breakage activity can be expressed. Alternatively, the above induction method may comprise a step of transforming a eukaryote having an inherent ploidy in such a way that a gene coding for a protein having double-stranded DNA breakage activity can be expressed, and a step of performing an artificial genome increase operation one or two or more times on the transformed eukaryote to thereby obtain a transformed eukaryote having the desired ploidy.

The various embodiments of the eukaryote, the protein having double-stranded DNA breakage activity, the ploidy and (poly)ploid, the protein having double-stranded DNA breakage activity, the expression of the gene coding for this protein and the artificial genome increase operation and the like explained above with reference to the method of inducing the eukaryotic organism population of this disclosure may also be applied to this parent eukaryotic organism and induction method therefor.

(Causing this Protein to Act within Cells of Parent Eukaryote)

Next, the way in which this protein is made to act in the cells of the parent eukaryote is explained. In the explanations below, when referring to action within the cells of the parent eukaryote, the mode of the parent eukaryote is not particularly limited. For example, when the parent eukaryote is a plant this may mean within the cells of a part of a plant such as cells or a tissue or organ, or cells of a seed, seedling, or individual plant grown from these, or of callus, without regard for the form of the plant. When the parent eukaryote is a yeast or other microorganism, it means that this protein is made to act within the cells of these.

To cause this protein to act within the cells of a parent eukaryote, conditions under which the double-stranded DNA breakage activity of this protein can be demonstrated are applied to this protein present within the cell. The protein may be made to act constantly (constitutively) with low activity, or it may be made to act deliberately and/or temporarily.

To cause this protein to act constantly, preferably this protein is expressed under the control of a suitable promoter (typically a constitutive promoter) for example, and the activity of this protein is regulated by means of the action temperature and action time so that the double-stranded DNA breakage activity of the protein does not become excessive. This is because the cells may die due to excessive double-stranded DNA breakage if this protein is expressed constantly. To achieve such activity regulation, a restriction enzyme derived from a thermophilic bacterium is used as this protein, and the action temperature is set at a temperature considerably lower than the optimum temperature of this restriction enzyme. Preferably, a restriction enzyme from a thermophilic bacterium is used.

For example, the action temperature depends on the type of this protein and the type of the eukaryote and the like, but can be set at 18° C. to 30° C. For example, the lower limit is more preferably 20° C. or higher, or still more preferably 22° C. or higher, and the upper limit is more preferably 28° C. or lower, or still more preferably 25° C. or lower.

Preferably this protein is made to act deliberately and temporarily. When this protein acts constantly, the cells may be damaged by excessive double-stranded DNA breakage. Thus, as discussed above, it is desirable to activate this protein by an operation in which this protein is expressed under the control of a suitable promoter, typically an inducible promoter.

With an inducible promoter, this protein can be expressed and made to act within cells with deliberate timing, and the action of this protein can generally be reduced or stopped by stopping induction. When this protein is expressed with an inducible promoter, the eukaryote is preferably grown or cultured at a temperature considerably lower than the optimum temperature for the double-stranded DNA breakage activity of this protein. For example, the temperature may be about 15° C. to 25° C. When this protein is expressed with an inducible promoter in the modification step using this protein, the eukaryote is preferably grown or cultured after the modification step under conditions that arrest the action of the inducible promoter.

After the double-stranded DNA breakage activity of this protein is artificially activated, it is preferably inactivated. The protein can thus be made to act effectively and in a more limited fashion. Thus, for example this protein can be activated and its activation can be stopped with deliberate timing by using a protein such as a restriction enzyme from a thermophilic bacterium of which optimum conditions for double-stranded DNA breakage activity are different from the ordinary growth (culture) conditions of the parent eukaryote. With such a protein, moreover, this protein can easily be made to act temporarily by growing (culturing) the parent eukaryote at a temperature below the temperature that fully activates this protein, and then growing (culturing) the parent eukaryote at or above the temperature for sufficient activation of this protein.

The double-stranded DNA breakage activity of this protein is preferably activated and made to act under conditions milder than the so-called optimum conditions at which activation of this protein is maximized. A cell population with a more diverse genome set composition can be constructed in this way. To apply this protein under such mild conditions, preferably this protein is activated for example at a temperature that is lower than the optimum temperature of the double-stranded DNA breakage enzyme, and within a temperature range that does not adversely affect cell activity. More preferably, this protein is activated at a temperature near the minimum temperature at which double-stranded DNA breakage activity can be expressed. Given 100% as the activity at the optimum temperature, a temperature near the minimum temperature at which double-stranded DNA breakage enzyme activity can be expressed may for example be a temperature at which this activity is about 5% to 30%, or preferably about 5% to 20%.

This acting temperature depends on the type of this protein and the type of eukaryote, but may be 18° C. to 45° C. for example. For example, the lower limit is more preferably 20° C. or higher, or still more preferably 22° C. or higher, or even more preferably 25° C. or higher, or still even more preferably 30° C. or higher, or yet even more preferably 35° C. or higher. For example, the upper limit is preferably 45° C. or lower, or more preferably 42° C. or lower, or still more preferably 40° C. or lower, or even more preferably 37° C. or lower, or still even more preferably 35° C. or lower. At this acting temperature, it is possible to efficiently modify a genome set in a eukaryote that is a polyploid with a ploidy greater than the inherent ploidy.

These temperature conditions are especially desirable for use with plants and microorganisms such as yeasts.

When the acting temperature of this protein is at or near the ordinary desirable growth temperature or culture temperature of the eukaryote, this protein can still be made to act transiently in the eukaryote by combining expression control of this protein by the action of an inducible promoter.

To apply this protein under mild conditions, depending on the type of protein and the type and acting temperature of the eukaryote, treatment on the protein can be performed under low activation conditions (for example, a temperature lower than the optimum temperature for the double-stranded DNA breakage activity of this protein) for about 30 minutes to an hour, or else for a relatively long period of time, such as at least 2 hours, or at least 3 hours, or more preferably at least 4 hours, or still more preferably at least 6 hours, or even more preferably at least 12 hours, or still even more preferably at least 24 hours, or yet even more preferably at least 36 hours, or most preferably at least 48 hours, or especially at least 60 hours, or ideally at least 72 hours.

Using TaqI as described above for example, depending on the type and timing of the parent eukaryote, cells expressing TaqI can be cultured or grown under temperature conditions of preferably 20° C. to 45° C., or more preferably 25° C. to 42° C., or still more preferably 30° C. to 42° C., or even more preferably 30° C. to 40° C., or still even more preferably 35° C. to 40° C., or yet even more preferably about 37° C. Preferably they are grown or cultured for a period of at least 2 hours, or more preferably at least 4 hours, or still more preferably at least 5 hours, or even more preferably at least 6 hours, or still even more preferably at least 12 hours, or yet even more preferably at least 24 hours, or most preferably at least 36 hours, or especially at least 48 hours, or more especially at least 60 hours, or ideally at least 72 hours. Such conditions are especially desirable in the case of plants and microorganisms such as yeasts.

The acting conditions such as the acting temperature and acting time of this protein can be determined appropriately by a person skilled in the art depending on this protein and microorganism used and the desired genome modification efficiency based on, for instance, the expression state of this protein, the growth (proliferation) state of the eukaryote, and an evaluation of genome rearrangement efficiency (evaluation using reporter genes or evaluation by ploidy histogram).

The modification step in which this protein is made to act within the cells of the parent eukaryote is performed in plants for example for a specific period of time on seeds collected before sowing from a parent eukaryote that is a parent plant that has been transformed so that it can express this protein, or between seeding and germination, or on a seedling after germination, or on a more developed plant. In yeasts for example, this protein is expressed or the expressed protein is activated for a specific period of time in a parent yeast that has been transformed so that it can express this protein.

When the parent eukaryote is a plant, this modification step preferably uses a seed or seedling. This is because this allows for easy multi-specimen treatment, and is convenient for obtaining a population of modified organisms. In the case of yeasts and the like, it is preferably performed during a period such as somatic cell division when germination is active (that is, during a period when the ploidy of the parent eukaryote is maintained).

In the modification step, when the parent eukaryote is a plant for example, a seed, seedling or developed plant or the like can be grown for 24 hours under temperature conditions of 37° C., and then returned to lower temperature growth conditions (for example, about 20° C. to 25° C. in the case of *Arabidopsis thaliana*).

When the parent eukaryote is a yeast, it may be maintained at a yeast culture condition of 37° C. for 24 hours, and then returned to a normal culture temperature (about 25° C. to 30° C.).

Performing this modification step causes genetic recombination to occur and a genome set reflecting the genetic recombination to be retained in each eukaryote subjected to the modification step. It is thus possible to obtain a population of eukaryotes having modified genome sets. The individual organisms in this eukaryote population have a variety of "modified genome sets" resulting from genetic recombinations occurring the original parent eukaryote population. The genome set composition of a eukaryote that has undergone this modification step is even more diverse because the parent eukaryote is a polyploid having a ploidy greater than the inherent ploidy, and because it has been treated with a protein having double-stranded DNA breakage ability.

For example, the genome sets of eukaryotes constituting a newly constructed eukaryote population obtained by this induction method tend to have acquired or increased chromosomes aneuploidy as a result of genetic recombination. The genome sets of eukaryotes may tend to exhibit deletion or duplication of part of a chromosome as a result of genetic recombination. Moreover, the genome sets of these eukaryotes also tend to have a reduced genome size due to loss or the like of some regions of the genome set, or an increased genome size due to duplication or the like of part of the genome set. Moreover, the genome sets of such eukaryotes tend to have one or two or more mutations.

By performing genetic modification on a parent eukaryote with tetraploid or greater ploidy in this modification step, it is possible to obtain a population with a genome set diversity greater than what is expected when this protein is made to act on a diploid parent eukaryote. That is, genetic recombination of chromosomal DNA is dramatically increased when the target is tetraploid or higher. Moreover, the resulting eukaryote shows a strong tendency towards genome size changes (size reduction and increase) and heteroploidy.

In general, growth suppression and the like tend to occur when a protein such as TaqI having double-stranded DNA breakage ability is made to act in a parent eukaryote by introducing a gene coding for that protein, but the degree of growth suppression that occurs in a at least tetraploid parent eukaryote tends to be less than when the TaqI gene or the like is applied to a diploid. That is, resistance to introduction of TaqI or the like can be conferred if the parent eukaryote has tetraploid or higher ploidy.

In general, ploidization tends to decrease the mass of a plant or other eukaryote, but this tendency is unexpectedly suppressed in the case of a eukaryote obtained from an organism with tetraploid or higher ploidy. It is thought that this is because the resulting eukaryote has decreased or increased chromosomal aneuploidy and/or genome size. This tendency is greater the greater the ploidy of the parent eukaryote. For example, although growth is greatly suppressed in the case of an octaploid parent eukaryote when this protein is not applied, the mass may be equal to or greater than that of the wild type when this protein is applied. This is also attributed to decreased or increased genome set size and/or chromosomal aneuploidy.

As explained above, with this induction method functional damage to chromosomes and genes due to genetic recombination can be suppressed and a eukaryote having a novel genome set composition due to genetic recombination can be obtained by causing a protein having double-stranded DNA breakage activity to act within the cells of a eukaryote having a doubled genome. It is thus possible to construct a eukaryote population with a diverse genome set composition. Consequently, with this induction method it is possible to efficiently exploit the advantages of chromosome doubling while simultaneously avoiding problems associated with chromosome doubling (genome size increase) in eukaryotes. It is thus possible to construct a population of a eukaryote that is also morphologically diverse.

In particular, quantitative traits and other traits associated with multiple genes can be efficiently improved by applying double-stranded DNA breakage activity to such a genome set with a large genome size.

Moreover, in this induction method one or two or more eukaryotes can be selected from the resulting eukaryote population as parent eukaryotes, and subjected to a further modification step, and these modification and selection steps may be performed repeatedly.

Thus, this induction method may be implemented as a production method including a modification step for producing a population of a eukaryote with a modified genome set.

(Method for Producing Modified Eukaryote)

The method for producing a modified eukaryote disclosed in the present Description may comprise a modification step in which a protein having double-stranded DNA breakage ability is made to act within the cells of a eukaryote that is a polyploid having a ploidy greater than the inherent ploidy to thereby modify the genome set of the eukaryote, and a step of selecting a target eukaryote based on any indicator from a population of the eukaryote carrying the modified genome set. With this method, a target eukaryote can be obtained efficiently because one or two or more target eukaryotes are selected from a highly diverse eukaryote population. Moreover, with this method efficient breeding is possible using the selected eukaryote. Consequently, this production method may be implemented as a method of breeding a eukaryote such as a plant or yeast. Breeding of subsequent progeny after a useful plant or yeast or the like has been obtained is something that can be accomplished by applying conventional known breeding techniques.

The various embodiments of the modification step in this production method explained above may be applied as is to the modification step in this method. The modification step and selection step may also be performed repeatedly in this method. That is, one or two or more selected eukaryotes may be subjected to further modification and selection steps as parent eukaryotes.

EXAMPLES

Examples embodying this disclosure of the present Description are explained below. However, the following examples are intended to explain this disclosure, not to limit their scope.

In the examples below, *Arabidopsis thaliana* was cultivated as follows unless otherwise specified. Seeds were sown on MS agar medium (Murashige and Skoog inorganic salts, 1% sucrose, 0.05% MES, 0.8% Agar), grown in a climate-controlled chamber at 22° C. with 16 hours of light and 8 hours of darkness at a light intensity of about 30 to 50 µmol/m$^2$/sec for three weeks, and then transplanted to pots 50 mm in diameter containing a super mix (Takii & Co., Ltd.). These were then cultivated for another 9 weeks at 22° C. with 16 hours of light and 8 hours of darkness at a light intensity of about 30 to 45 µE/m²/s, after which irrigation was stopped and cultivation was continued for a further 2 weeks. After cultivation the plants were dried and weighed to obtain dry plant weights.

First Example (Construction of TaqI Gene Plant Expression Vectors)

pBI 35S:TaqI-NLS having the TaqI gene disposed downstream from the cauliflower mosaic virus 35S promoter and pBI AtSIG2:TaqI-NLS having the TaqI gene disposed downstream from the *Arabidopsis thaliana* sigma factor AtSIG2 promoter were each constructed by the methods disclosed in Japanese Patent Application Laid-open No. 2011-160798 (paragraphs 0121-0142) as TaqI gene plant expression vectors. A nuclear localization signal (NLS) was also provided at the C-end of the TaqI coding region of the plasmids.

Second Example (Introduction of 35S:TaqI Gene into *Arabidopsis Thaliana*)

An *Agrobacterium* (C58C1 strain) carrying pBI 35S:TaqI-NLS was prepared in accordance with Japanese Patent Application Laid-open No. 2011-160798. This *Agrobacterium* was used to introduce the 35S:TaqI gene into the *Arabidopsis thaliana* 1406 strain (EMBO Journal (2006)25, 5579-5590). The 1406 strain comprises a GUS reporter gene with an Inverted repeat structure introduced into the wild-type *Arabidopsis thaliana* ecotype Col-0 strain, and is constructed so that the GUS gene is expressed when homologous recombination occurs within the GUS gene. This system is used for quantitative analysis of homologous recombination.

The implanter method was used as the transformation method. That is, the plant expression vector prepared in the First Example was introduced into the *Agrobacterium tumefaciens* C58C1 strain by the electroporation method (Plant Molecular Biology Manual, Second Edition, B. G. Stanton and A. S. Robbert, Kluwer Academic Publishers 1994). Next, the *Agrobacterium tumefaciens* with the introduced plant expression vector was introduced into the wild-type *Arabidopsis thaliana* ecotype Col-0 strain by the infiltration method described by Clough et al (Steven J. Clough and Andrew F. Bent, 1998, The Plant Journal 16, 735-743).

The transformed *Arabidopsis thaliana* was grown at 22° C. with 16 hours of light and 8 hours of darkness at a light intensity of about 30 to 50 µmol/m²/sec, and T1 seeds were collected. The collected T1 seeds were aseptically sown on modified MS agar medium (sucrose 10 g/L, MES (2-Morpholinoethanesulphonic acid) 0.5 g/L, agar (for bacterial culture: Wako Pure Chemical Industries, Ltd.) 8 g/L) containing kanamycin (50 mg/L), and grown for 2 weeks at 22° C. with 16 hours of light and 8 hours of darkness at a light intensity of about 30 to 45 µmol/m²/sec, and kanamycin-resistant individuals were selected to obtain the transformant TCL878.

Third Example (Preparation of Tetraploid and Octoploid *Arabidopsis Thaliana* Plants)

In this example, a genome increase operation was performed using colchicine to obtain tetraploid and octaploid plants.

Plants of the *Arabidopsis thaliana* ecotype Col-0 wild strain and 1406 strain and the pBI 35S:TaqI-NLS-introduced line obtained in the Second Example were grown for 3 weeks in sterile medium containing 1% sucrose, and then immersed for 1 to 10 minutes in a 0.01% colchicine solution containing 0.05% Triton-X. These were then transplanted into pots 50 mm in diameter containing a super mix (Takii & Co., Ltd.) and grown in a climate-controlled chamber at 22° C. with 16 hours of light and 8 hours of darkness at a light intensity of about 30 to 50 µmol/m²/sec, and seeds were obtained after 8 weeks of growth. In the next generation plants, the genome ploidy was investigated by a method using staining of the nuclei by DAPI and flow cytometry, and the tetraploid plants were selected to obtain Col-0_P4, 1406_P4, and TCL878_P4C2. The resulting tetraploid plants were then treated in the same way with colchicine solution, and octoploidized flower stems were selected to obtain Col-0_P8, 1406_P8 and TCL878_P8.

Measurement of plant ploidy by flow cytometry was accomplished as follows.

Rosette leaves or stem leaves of bolted flower stems of the of the plant 3 weeks after germination or were excised, and the rosette leaves were immersed in 400 µl of a mixture of the nuclear staining solution and nuclear extraction solution of a CyStain UV plant DNA reagent kit (Partec), and finely cut with a razor (about 100 cuts/cm²). The plant cell residue in the extract was then removed with 50 µm of CellTrics (registered trademark) (Partec). The resulting nuclear solution was measured with a Cell Lab Quanta SC MPL (Beckman Coulter, Inc.).

Fourth Example (Introduction of SIG2:TaqI Tene into *Arabidopsis Thaliana*)

*Agrobacterium* carrying pBI AtSIG2:TaqI-NLS was used to introduce the SIG2:TaqI gene into the Col-0_P4 strain prepared in the Third Example. An implanter method similar to that of the Second Example was used as the transformation method. Seeds obtained after infection by the *Agrobacterium* were sown on MS agar medium containing kanamycin (Murashige and Skoog inorganic salts, 1% sucrose, 0.05% MES, 0.8% Agar, 50 mL/L kanamycin sulfate). These were grown for 2 weeks in a climate-controlled chamber at 22° C. with 16 hours of light and 8 hours of darkness at a light intensity of about 30 to 50 µmol/m²/sec, and kanamycin resistant individuals were selected to obtain a transformant TS3055.

Fifth Example (Morphological and Genome Structure Changes in 35S:TaqI Gene-Introduced *Arabidopsis Thaliana* Tetraploid Line Progeny Plants)

Seedlings of the tetraploid TCL878_P4C2 line having the 35S:TaqI gene were heat treated for 1 day at 37° C. 1 week after germination and then grown, and seeds were collected. The resulting TCL878_P4C2 line progeny seeds and the control strain 1406_P4 were sown and grown, and their morphologies observed. The results are shown in FIG. 2.

Figure 2:
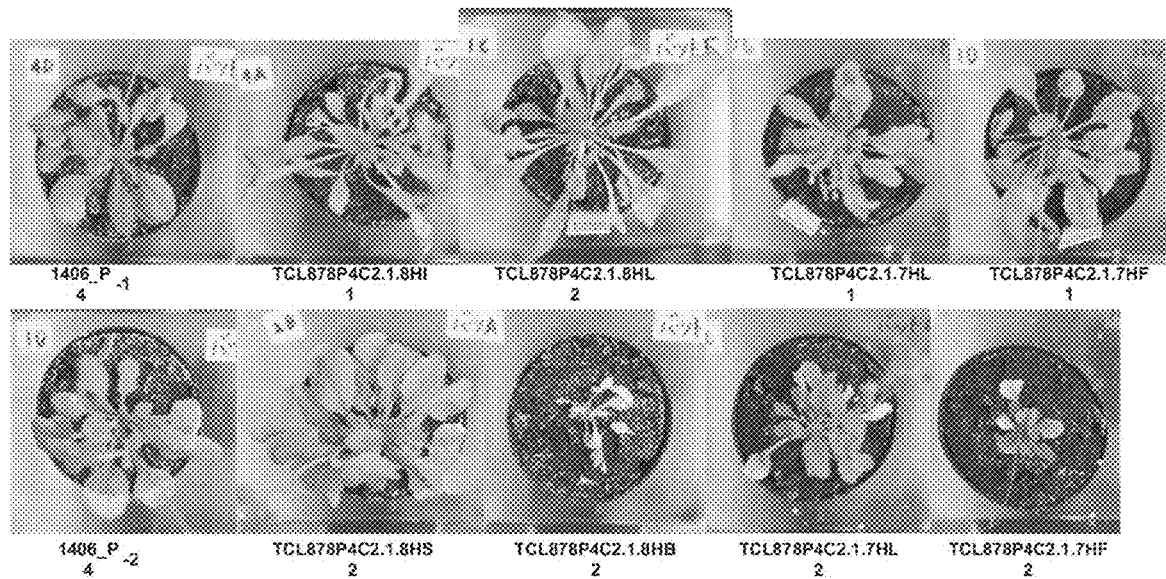
FIG. 2 shows morphological changes in a tetraploid control strain and in tetraploid TaqI-introduced lineage plants.

As shown in FIG. 2, a variety of morphological changes were observed in the TCL878_P4C2 line progeny, including enlargement of individual plants due to leaf enlargement and petiole elongation, leaf thinning, leaf miniaturization, promotion of flower formation, delay of flower formation, and promotion and suppression of leaf aging and the like.

Next, genome DNA was extracted from the plants. Genome copy number polymorphism was analyzed by tiling array using the extracted genome DNA. The copy number polymorphism analysis was performed as follows. The results are shown in FIG. 3.

(Tiling Array Analysis for Analyzing Chromosome Copy Numbers in TaqI Gene-Introduced *Arabidopsis Thaliana* Chromosomes)

The *Arabidopsis thaliana* tiling array was designed with an eArray system from Agilent Technologies. At_tilling_400K_v3.2 was designed with 381,815 individual 60-mer probes arrayed with an average spatial resolution of about 314 nt on the *Arabidopsis thaliana* genome. Similarly, At_tilling_180K_v4 was designed with 177,170 60-mer probes arrayed with an average spatial resolution of about 677 nt on the *Arabidopsis thaliana* genome. The tiling arrays were performed according to the protocols from Agilent Technologies. Scanning of the tiling arrays was performed with an Agilent G2565CA microarray scanner (Agilent Technologies). Fluorescent signal extraction and quantification were performed with Feature Extraction software. The relative levels were determined by the formula (Relative level=$Log_{10}$(Cy5(sample)/Cy3(control))), and the average value of the relative levels of 20 continuous probes on the chromosome was determined and shown in the figure.

Figure 3:
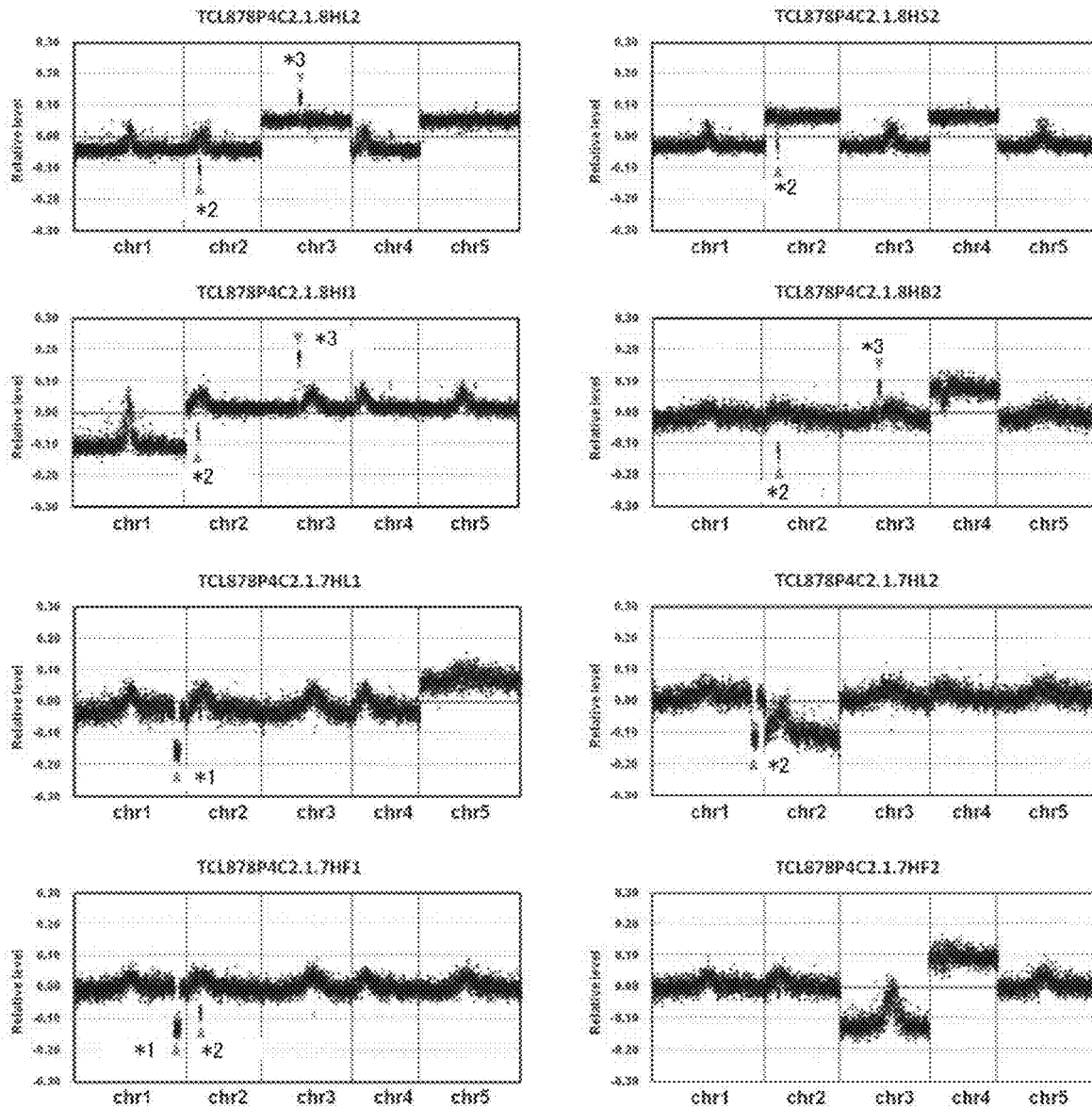
FIG. 3 shows a copy number analysis by tiling array of the chromosomes of morphologically altered strains of tetraploid TaqI-introduced lineage plants.

As shown in FIG. 3, frequent chromosomal aneuploidy and local increases and decreases in the number of genome copies were detected in the TCL878_P4C2 line progeny. These results show that individual plants exhibiting more diverse changes in genome set composition and phenotype can be prepared by combining genome doubling with the effects of a protein having double-stranded DNA breakage activity.

Sixth Example (Morphological Changes in SIG2:TaqI Gene-Introduced *Arabidopsis Thaliana* Tetraploid Line Progeny Plants)

Morphological changes were observed in the same way as in the Fifth Example using TS3055 line, a tetraploid line carrying the SIG2:TaqI gene, in order to confirm the effects in tetraploid plants with different promoters. T2 generation plants of transformants of the TS3055 line, a tetraploid line carrying the SIG2:TaqI gene obtained in the Fourth Example, were grown and their morphologies were compared with that of the Col-0_P4 strain as a control strain. The results are shown in FIG. 4.

Figure 4:
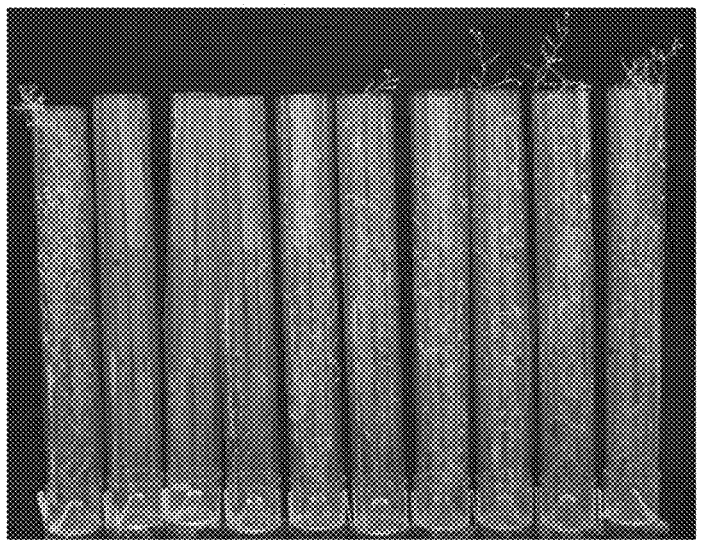
FIG. 4 shows a plant 9 weeks after sowing of the TS3055 line T2 generation.

As shown in FIG. 4, in comparison with the Col-0_P4 strain the plants of the TS3055 line exhibited various morphological changes such as promotion or delay of flower formation, leaf enlargement, and promotion or suppression of stem elongation. These results show that morphological changes can be induced by expressing TaqI with different promoters.

Seventh Example (Improved Resistance to TaqI Expression in Tetraploid Plants)

1 week after sowing of a TaqI gene-introduced *Arabidopsis thaliana* diploid line (TCL878) selected in the Second Example, a tetraploid line (PCL878_P4) selected in the Third Example and a control diploid line (1406) and tetraploid line (1406_P4), the plants were heat treated for 1 day at 37° C., and then cultivated continuously for 14 weeks, and the dry weights were measured. The results are shown in FIG. 5.

Figure 5:
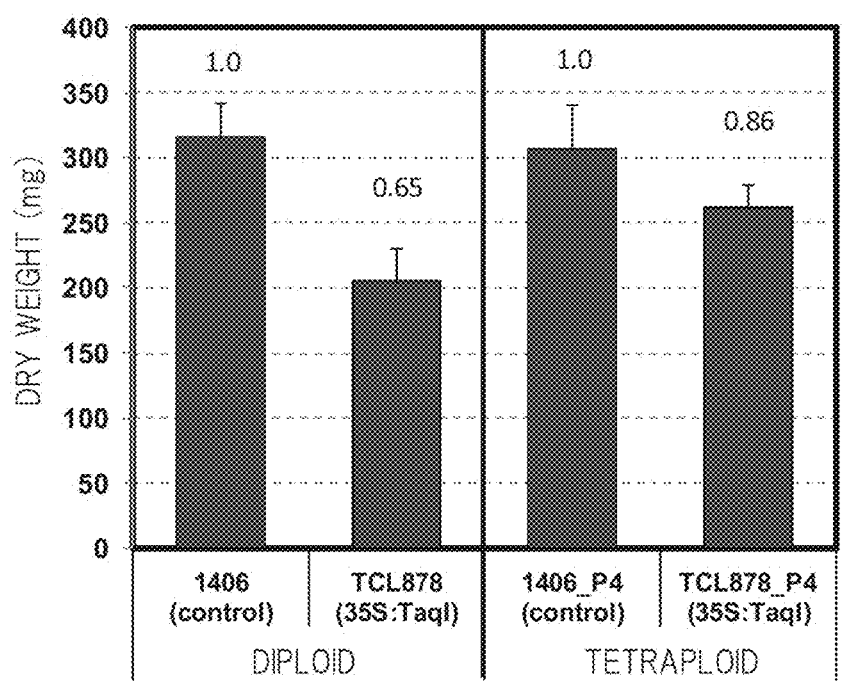
FIG. 5 shows dry weights after 14 weeks of growth following heat treatment of diploid and tetraploid TaqI lineage plants.

As shown in FIG. 5, in the diploid plants the dry weight of the TaqI gene-introduced line was much lower (0.65) than in the control strain. In the tetraploid plants, on the other hand, the dry weight of the TaqI gene-introduced line was 0.86 in comparison with the control, so the decrease in dry weight was less than with the diploid plants. This shows that the tetraploid plants had more resistance to TaqI gene expression than the diploid plants.

Eighth Example (Genome Ploidy of 35S:TaqI or SIG2:TaqI Gene-Introduced Tetraploid *Arabidopsis Thaliana* Lines)

To investigate the effects on plant ploidy of double-stranded DNA breakage induced by expression of the TaqI gene, plant ploidy was measured by methods similar to those of the Third Example in Col-0, Col-0_P4, 1406, TCL878, TS3055 and TCL878_P4 (progeny of plants heat treated for 1 day at 37° C. 1 week after budding), and histograms were prepared. The results are shown in FIG. 6.

Figure 6:
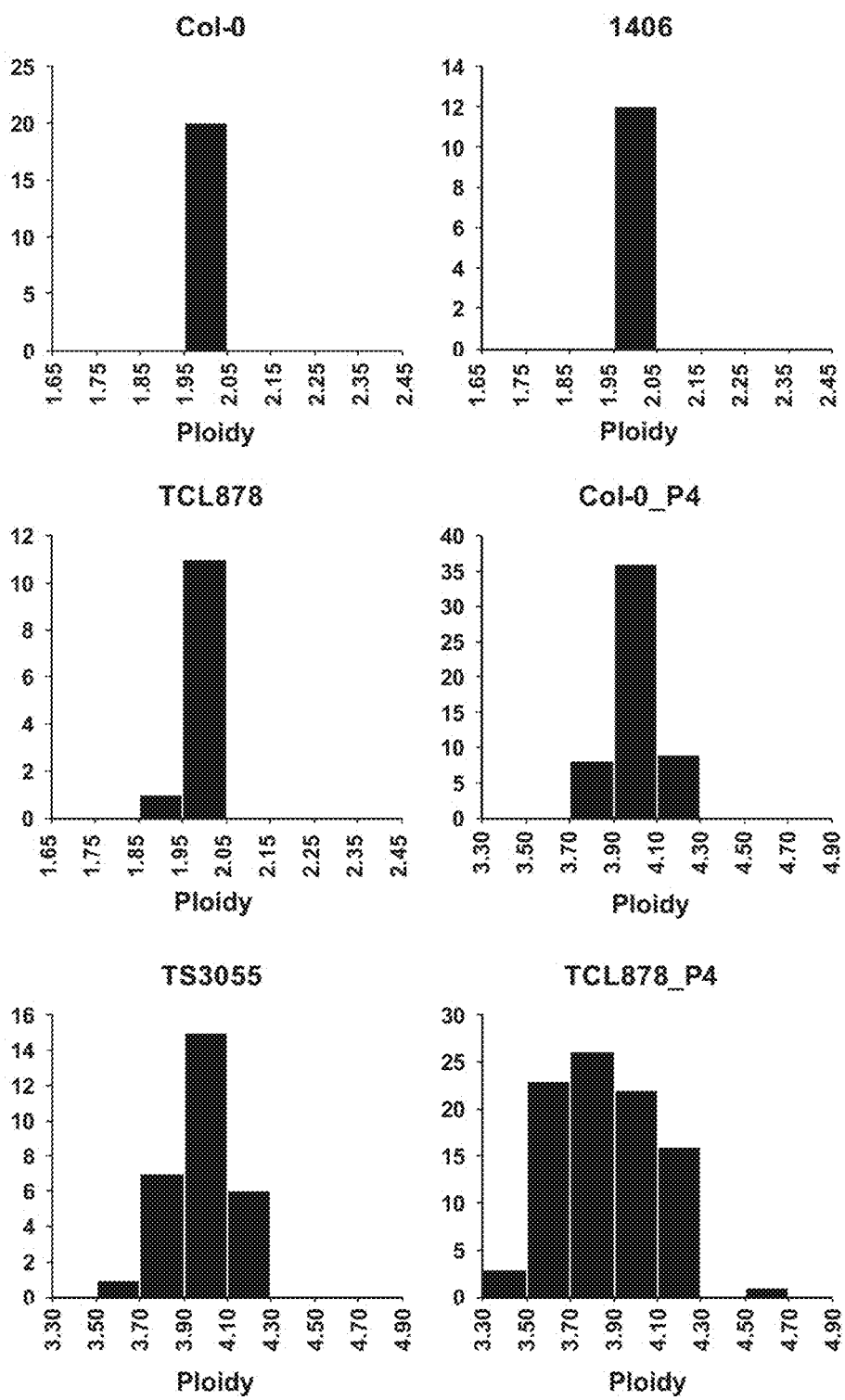
FIG. 6 shows ploidy histograms of diploid and tetraploid wild strains and diploid and tetraploid TaqI-introduced lines.

As shown in FIG. 6, in the tetraploid lines TS3055 (AtSIG2 promoter) and TCL878_P4 (35S promoter) having the introduced TaqI gene, there was an increase in the frequency of individuals with increased or reduced ploidy. Moreover, in this example the histograms showed an overall move towards decreased ploidy, and the genome size decreased. From this it appears that the compositions of the genome sets fluctuated greatly in the tetraploid lines.

Ninth Example (Dry Weight and Ploidy of TaqI Gene-Introduced *Arabidopsis Thaliana* Octaploid Line Progeny Plants)

Seeds fruited on the flower stalks of the TaqI gene-introduced *Arabidopsis thaliana* octaploid line selected in the Third Example were sown and grown. The growing conditions of these plants were observed, and the ploidy of each plant and the dry weight after 14 weeks of cultivation were measured. Ploidy was also measured with a flow cytometer as in the Second Example. For one of the octaploid line progeny, the TCL878_P8-5#3 strain, the number of copies of the gene was investigated by tiling array as in the Fifth Example. The results are shown in FIGS. 7 to 9.

Figure 7:
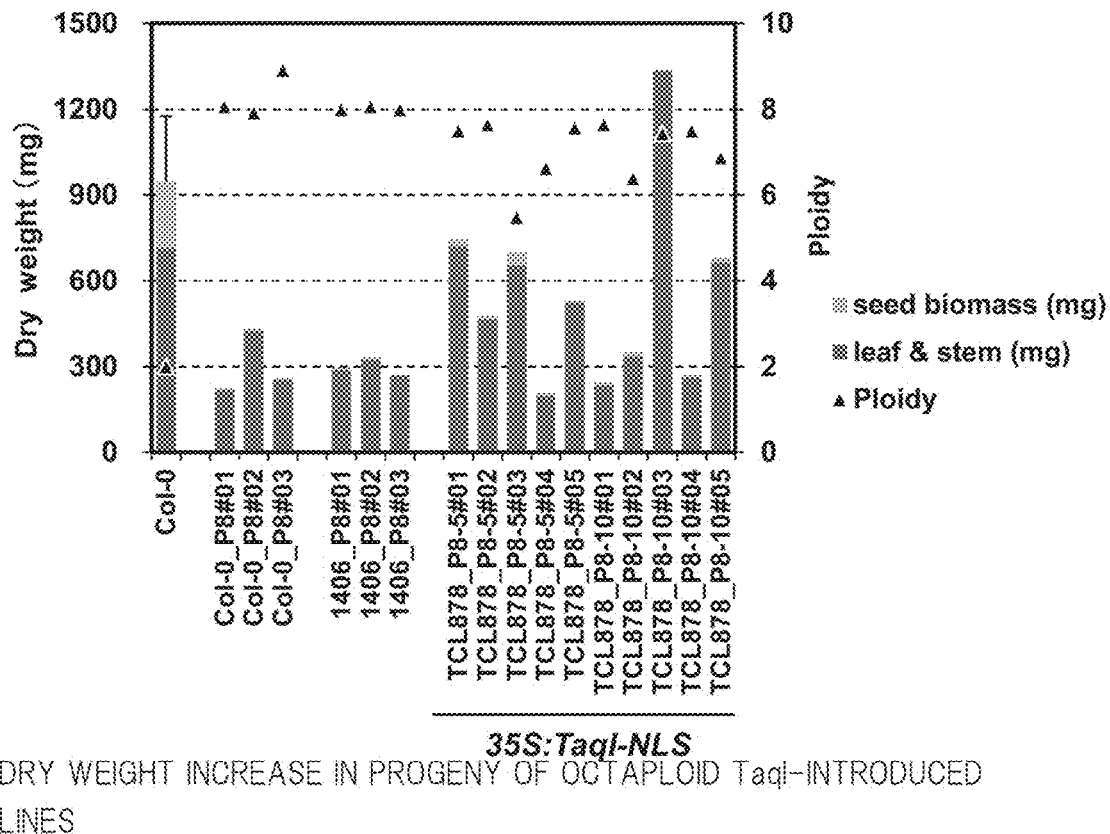
FIG. 7 shows dry weight increase in octaploid TaqI-introduced line progeny.
Figure 8:
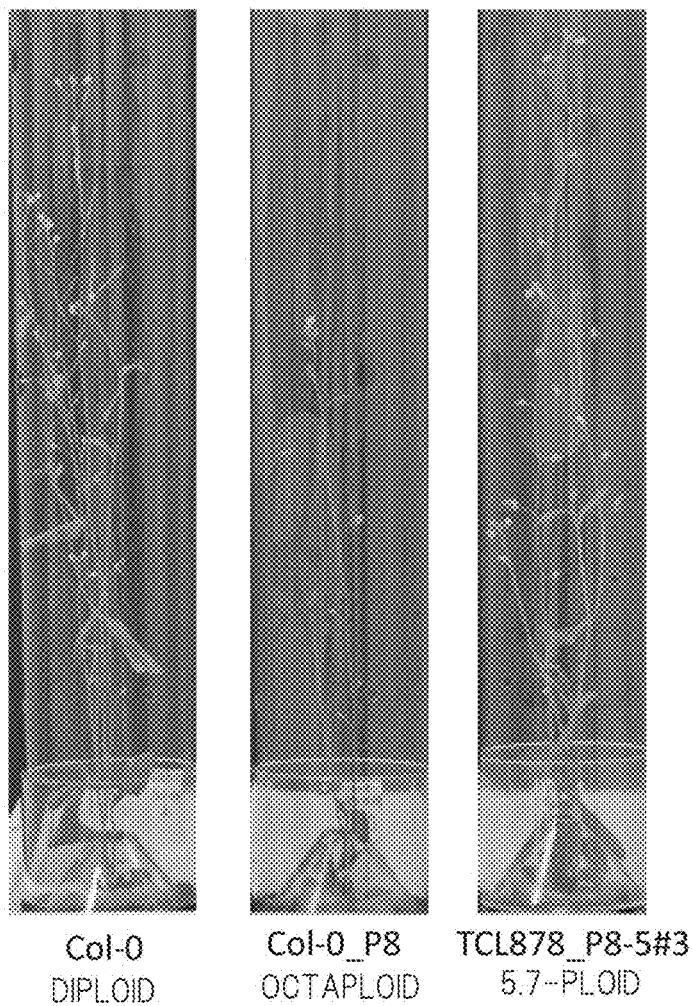
FIG. 8 shows the growth of an octaploid wild strain and a TaqI-introduced octaploid line 40 days after sowing.

As shown in FIG. 7, the octaploid plants Col-0_P8 and 1406_P8 prepared from the Col-0 wild strain and 1406 control strain had dramatically reduced dry weights in comparison with the wild strain. This is attributed to polyploidy syndrome. On the other hand, the plant of the octaploid TCL878_P8 line prepared from the 35S:TaqI gene-introduced line tended to do better in comparison with Col-0_P8 and 1406_P8, and in the TCL878_P8-10#3 line the dry weight was even greater than in the diploid Col-0 wild strain.

FIG. 7 also shows ploidy, which was roughly octaploid in Col-0_P8 and 1406_P8, while many plants in the TCL878_P8 line exhibited ploidy lower than octaploid. In particular, the genome size of the TCL878_P8-5#3 strain fell to the equivalent of 5.7-ploid. As shown in FIGS. 7 and 8, moreover, this line exhibited good growth in comparison with Col-0_P8.

Figure 9:
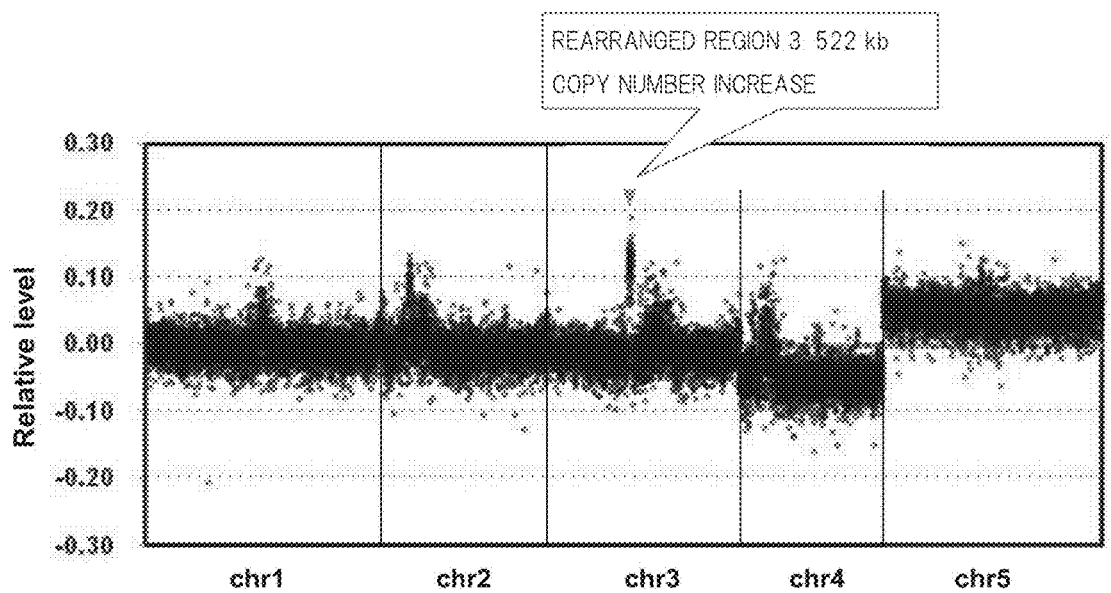
FIG. 9 shows a copy number analysis by tiling array of the TCL878_P8-5#3 chromosome.

According to a gene copy number analysis of the TCL878_P8-5#3 strain by tiling array as shown in FIG. 9, there were 6 copies of chromosome 1, chromosome 2 and chromosome 3, 5 copies of chromosome 4 and 7 copies of chromosome 5, indicating chromosome aneuploidy with different copy numbers of each chromosome. In the upper arm of chromosome 3, moreover, a 522 kbp region had two more copies than the surrounding region, for a total of about 8 copies.

From the above, it appears that a population expressing diverse genome set compositions and morphologies can be constructed by applying a double-stranded DNA breakage enzyme to a polyploid line. Moreover, applying a double-stranded DNA breakage enzyme to a polyploid line not only confers chromosome aneuploidy, but also reduces genome size, with the result that problems due to chromosome set increase are suppressed.

Tenth Example (Preparation of TaqI Gene Yeast Expression Vector)

Figure 10:
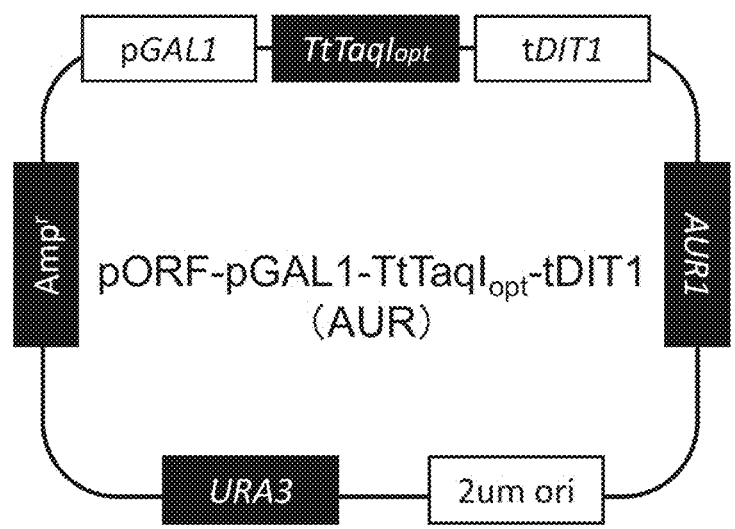
FIG. 10 shows an outline of the structure of a TaqI gene yeast expression vector.

As shown in FIG. 10, pORF-pGAL1-TtTaqI-tDIT1 (AUR) having a yeast codon optimized TaqI gene (TtTaqI opt) and a 3'UTR (tDIT1) of a DIT1 protein from *Saccharomyces cerevisiae* disposed downstream from a galactose inducible promoter (pGAL1) was used as the TaqI gene yeast expression vector.

Eleventh Example (Preparation of Yeast for Evaluating Genome Rearrangement)

Figure 11:
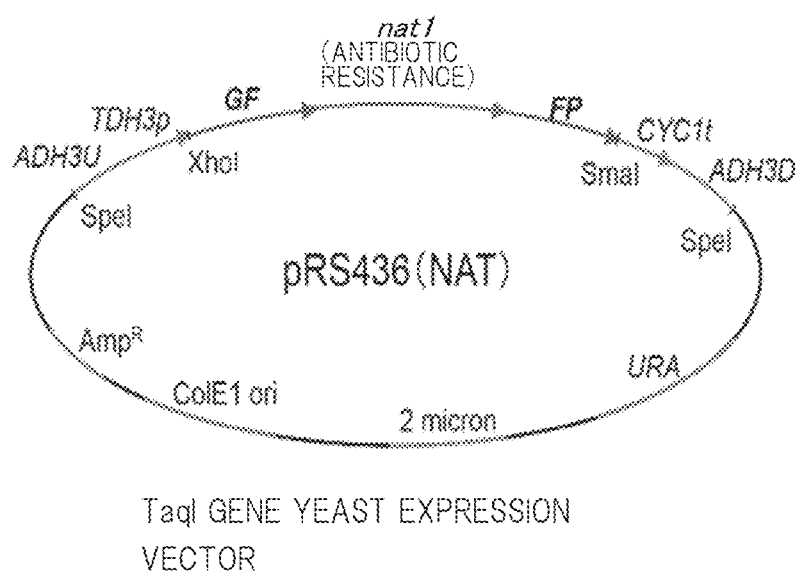
FIG. 11 shows construction of a plasmid containing the GF-FP reporter gene for evaluating genome rearrangement efficiency.
Figure 12:
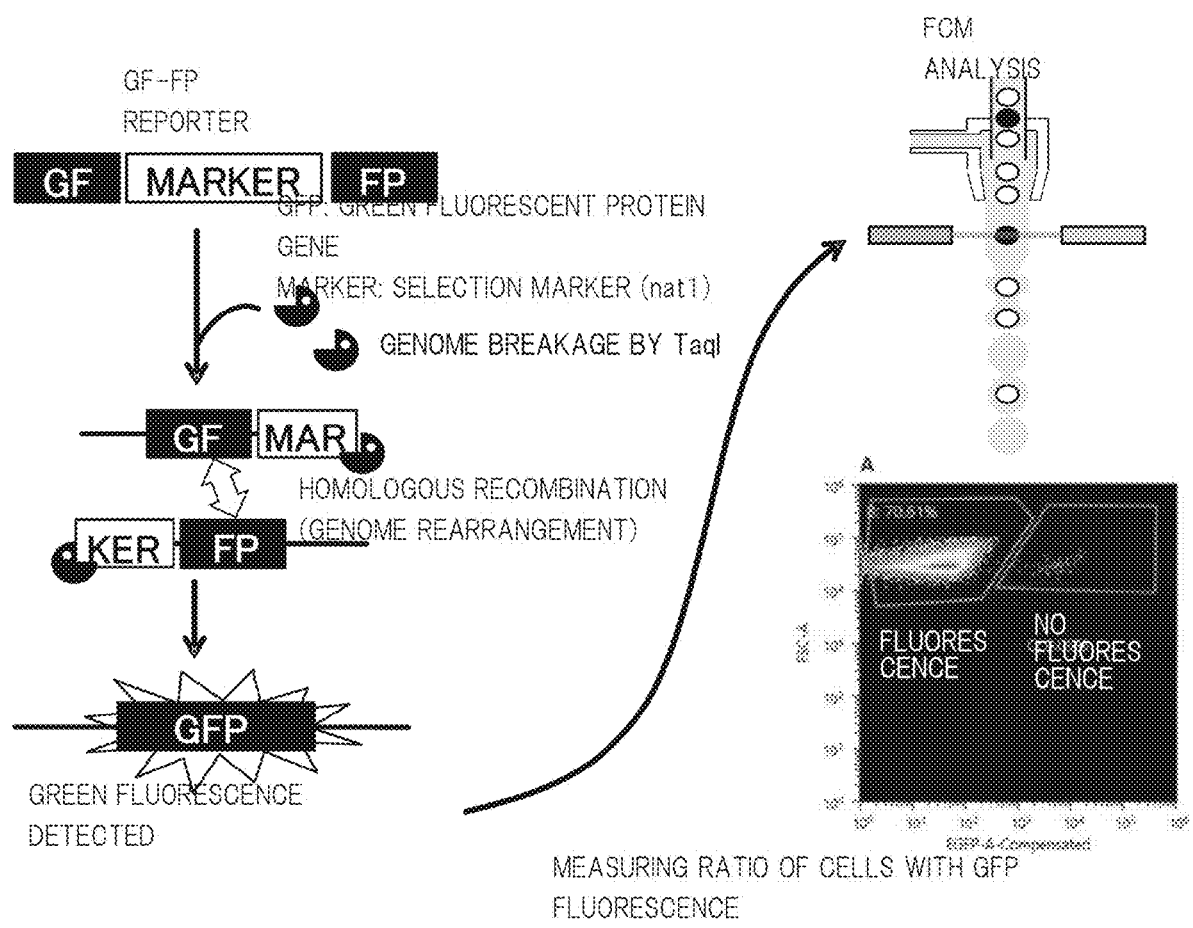
FIG. 12 shows an outline of a genome rearrangement evaluation method using the GF-FP reporter gene.

As shown in FIG. 11, a GF-FP reporter gene for evaluating genome rearrangement efficiency is designed with about 600 bp of the N-end and 600 bp of the C-end of green fluorescent protein (GFP) on either side of an antibiotic Nourseothricin resistance marker (nat1). Using this cassette, genome rearrangement can then be detected by flow cytometry or the like because the yeast emits green fluorescence when double-stranded DNA breakage by TaqI causes homologous recombination between GF and FP, resulting in reconstruction of the full-length GFP gene (see FIG. 12).

Strains having the GF-FP reporter gene introduced into ADH3 gene upstream regions (3000 bp to 2000 bp upstream from the transcription start point) of the *S. cerevisiae* strains BY4741 and BY4742 were called a BY4741+GFP strain and a BY4742+GFP strain. A BY4741+GFP(LEU) strain, BY4741+GFP(HIS) strain, BY4742+GFP(LEU) strain and BY4742+GFP(HIS) strain were also prepared each having the LEU2 gene or HIS3 gene from *S. cerevisiae* S288C complementing the leu2 gene and his3 gene of that strain.

Twelfth Example (Study of TaqI Expression Induction Conditions)

The TaqI gene yeast expression vector pORF-pGAL1-TtTaqIopt-tDIT1(AUR) prepared in the Tenth Example was transformed into the BY4741+GFP(HIS) strain prepared in the Eleventh Example to obtain (BY4741+GFP(HIS)+TaqI). This was cultured overnight at 30° C. using YPD medium with glucose as the sugar source (10 g/L Yeast extract, 20 g/L Peptone, 20 g/L Glucose)+0.5 mg/L aureobasidin A (AbA), after which the medium was replaced with YPG medium with galactose as the sugar source (10 g/L Yeast extract, 20 g/L Peptone, 20 g/L Galactose)+0.5 mg/L AbA medium, and the cells were cultured overnight at 20° C., 22.5° C., 25° C., 27.5° C. and 30° C. to induce TaqI expression. To measure the level of TaqI expression at each temperature, SDS-PAGE was performed with the cell amounts aligned, and Western blotting was performed using an anti-TaqI antibody. The results are shown in FIG. 13.

Figure 13:
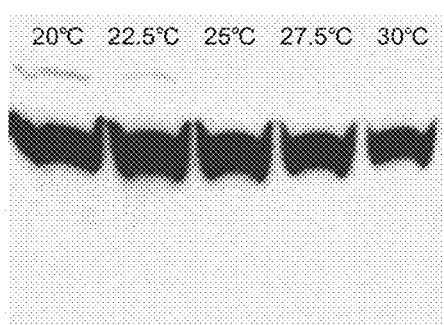
FIG. 13 compares the amount of TaqI expression using a BY4741+GFP(HIS) strain at various induction temperatures.
Figure 13:
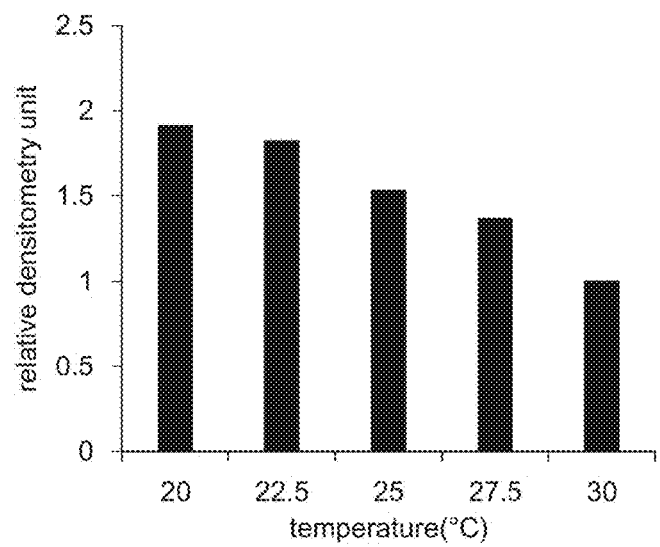

As shown in FIG. 13, the amount of TaqI expression was greatest when expression was induced at 20° C. Comparing the viable cell rates, the viable cell rate declined as the temperature rose, and even at 30° C. TaqI was activated but cell death occurred due to genome breakage.

Thirteenth Example (Evaluation of Genome Rearrangement Efficiency Due to Transient Heat Treatment)

Figure 14:
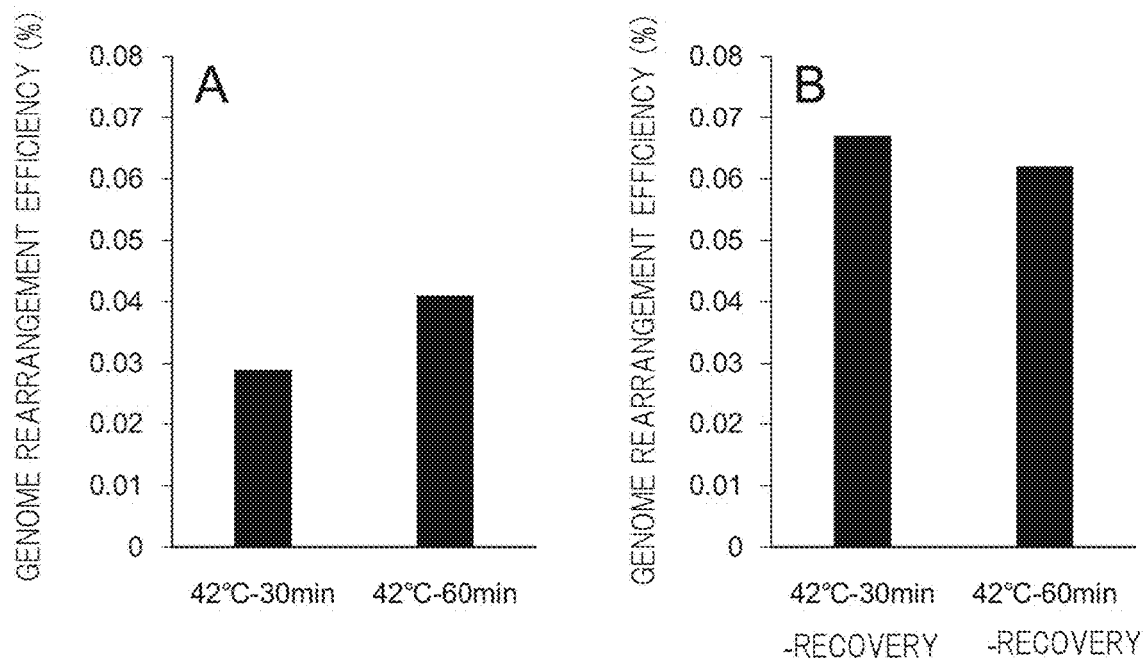
FIG. 14 shows genome rearrangement efficiency due to transient heat treatment using the BY4741+GFP(HIS) strain, with A showing rearrangement efficiency immediately after heat treatment, and B showing restructuring efficiency after recovery culture.

TaqI expression was induced at 20° C. as in the Twelfth Example using the BY4741+GFP(HIS)+TaqI strain. TaqI activation was promoted transiently by performing 30 minutes or 60 minutes of heat treatment at 42° C., and genome rearrangement efficiency was calculated by measuring the ratio of cells with GFP fluorescence in $1\times10^5$ cell by flow cytometry. The results are shown in FIG. 14A. The resulting genome rearrangement efficiency was 0.03% to 0.04%. As shown in FIG. 14B, the genome rearrangement efficiency rose to 0.06% to 0.07% when the medium was replacement with YPD medium and recovery culture was performed for 18 hours after heat treatment.

Fourteenth Example (Evaluation of Genome Rearrangement Efficiency Due to Mild Heat Treatment)

Using the BY4741+GFP(HIS)+TaqI strain, the medium was replaced with YPG+0.5 mg/L AbA medium as in the Twelfth Example, TaqI expression was induced at 20° C., 25° C., 30° C. and 35° C., and mild TaqI activation was performed. After 5, 23 and 46 hours the yeast was collected, and genome rearrangement efficiency was measured by flow cytometry as in the Thirteenth Example. The results are shown in FIG. 15.

Figure 15:
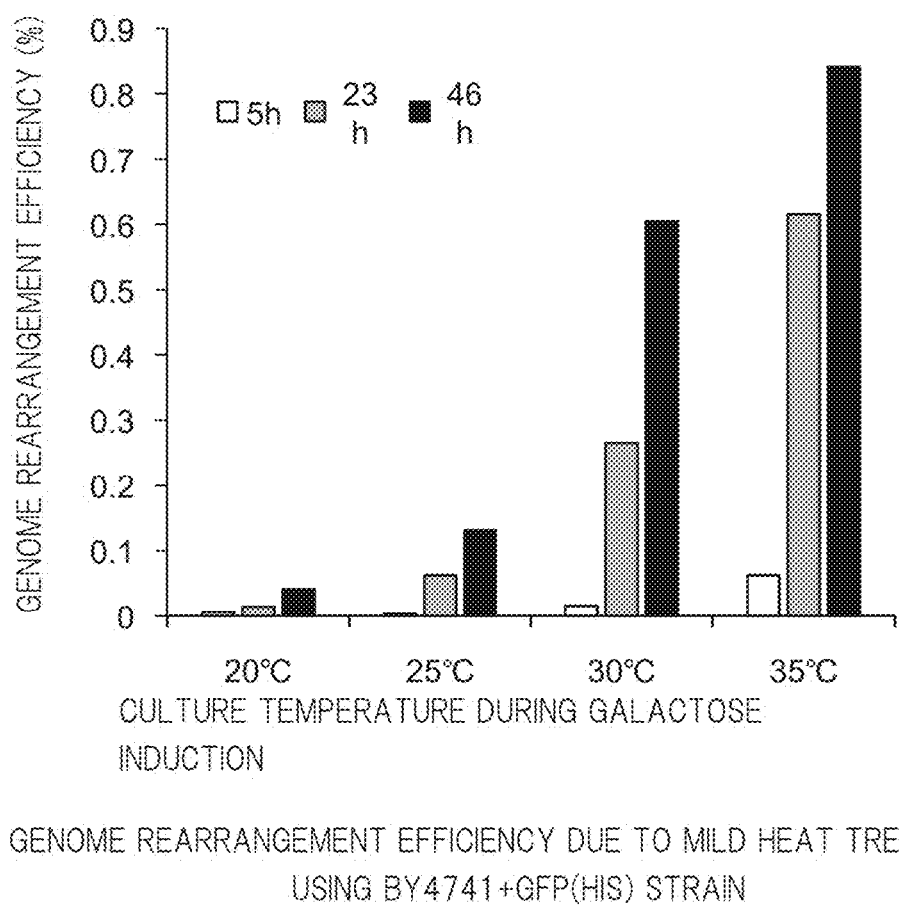
FIG. 15 shows genome rearrangement efficiency due to mild heat treatment using the BY4741+GFP(HIS) strain.

As shown in FIG. 15, genome rearrangement efficiency increased with the passage of time at each temperature. The genome rearrangement efficiency rose especially at 30° C. or higher, to roughly 10 to 20 times the value obtained with transient heat treatment.

Fifteenth Example (Preparation of Diploid Yeast and Tetraploid Yeast)

The BY4741+GFP(LEU) strain was conjugated with the BY4742+GFP(LEU) strain and the BY4741+GFP(HIS) strain with the BY4742+GFP(HIS) strain by ordinary methods, and cultured for 5 days at 30° C. on SD-Met-Lys agar plates. The grown colonies were separated into singles, the amount of genome DNA was measured by flow cytometry, and strains that were confirmed to be diploid were called the BY4743+GFP(LEU) and BY4743+GFP(HIS) strains.

The BY4743+GFP(LEU) and BY4743+GFP(HIS) strains were subjected to cell fusion to prepare a tetraploid yeast. Cell fusion was performed by the protoplast-PEG method. Colonies grown on SD-Leu-His agar plates were taken as cell fusion candidate strains. The grown colonies were separated into singles, the amount of genome DNA was measured by flow cytometry, and a strain that was confirmed to be tetraploid was taken as the BY4744+GFP(LH) strain.

Sixteenth Example (Measuring Genome Rearrangement Efficiency Using Doubled Yeasts)

The TaqI gene yeast expression vector pORF-pGAL1-TtTaqIopt-tDIT1(AUR) prepared in the Tenth Example was transformed into the doubled yeasts prepared in the Eleventh and Fourteenth examples. Using the resulting transformants, the medium was replaced with YPG+0.5 mg/L AbA medium as in the Twelfth Example, and TaqI expression was induced at 35° C. while TaqI was mildly activated. After 22 hours the yeasts were collected, and genome rearrangement efficiency was measured by flow cytometry as in the Thirteenth Example. The results are shown in FIG. 16.

Figure 16:
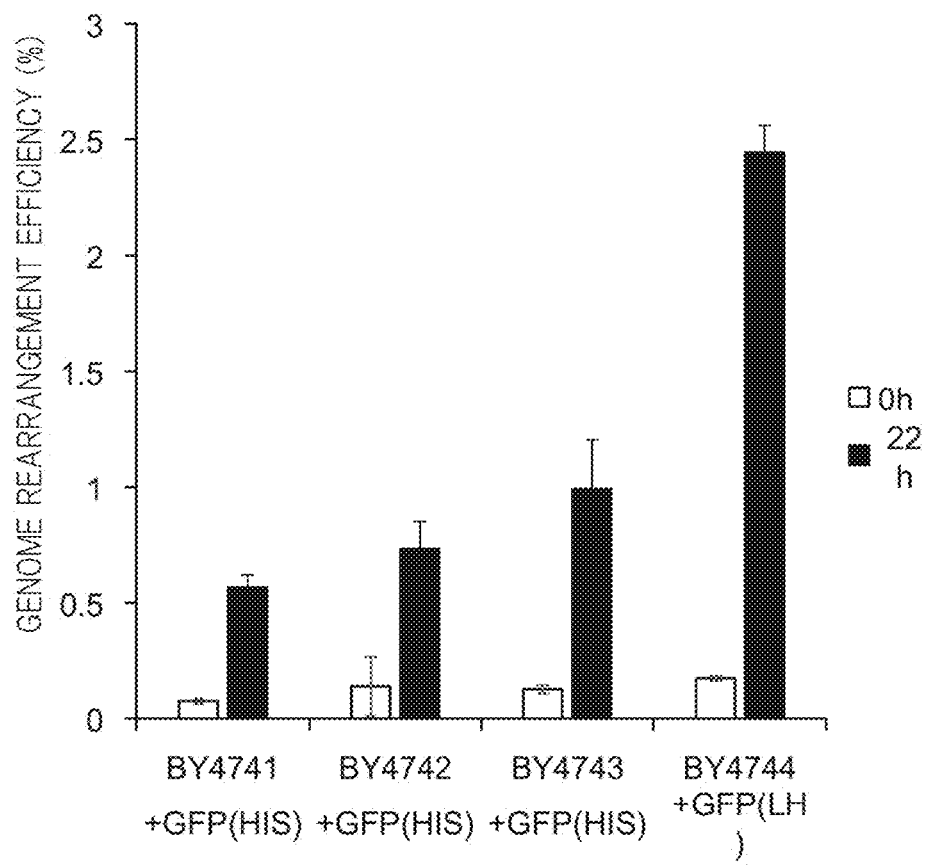
FIG. 16 compares genome rearrangement efficiency using haploid, diploid and tetraploid yeasts.

As shown in FIG. 16, genome rearrangement efficiency was 0.5% to 0.75% with the haploid yeast, but increased to 1.0% with the diploid yeast and 2.5% with the tetraploid yeast, showing the genome doubling increased genome rearrangement efficiency.

Seventeenth Example (Changes in Ploidy Due to Genome Rearrangement of Doubled Yeasts)

Figure 17:
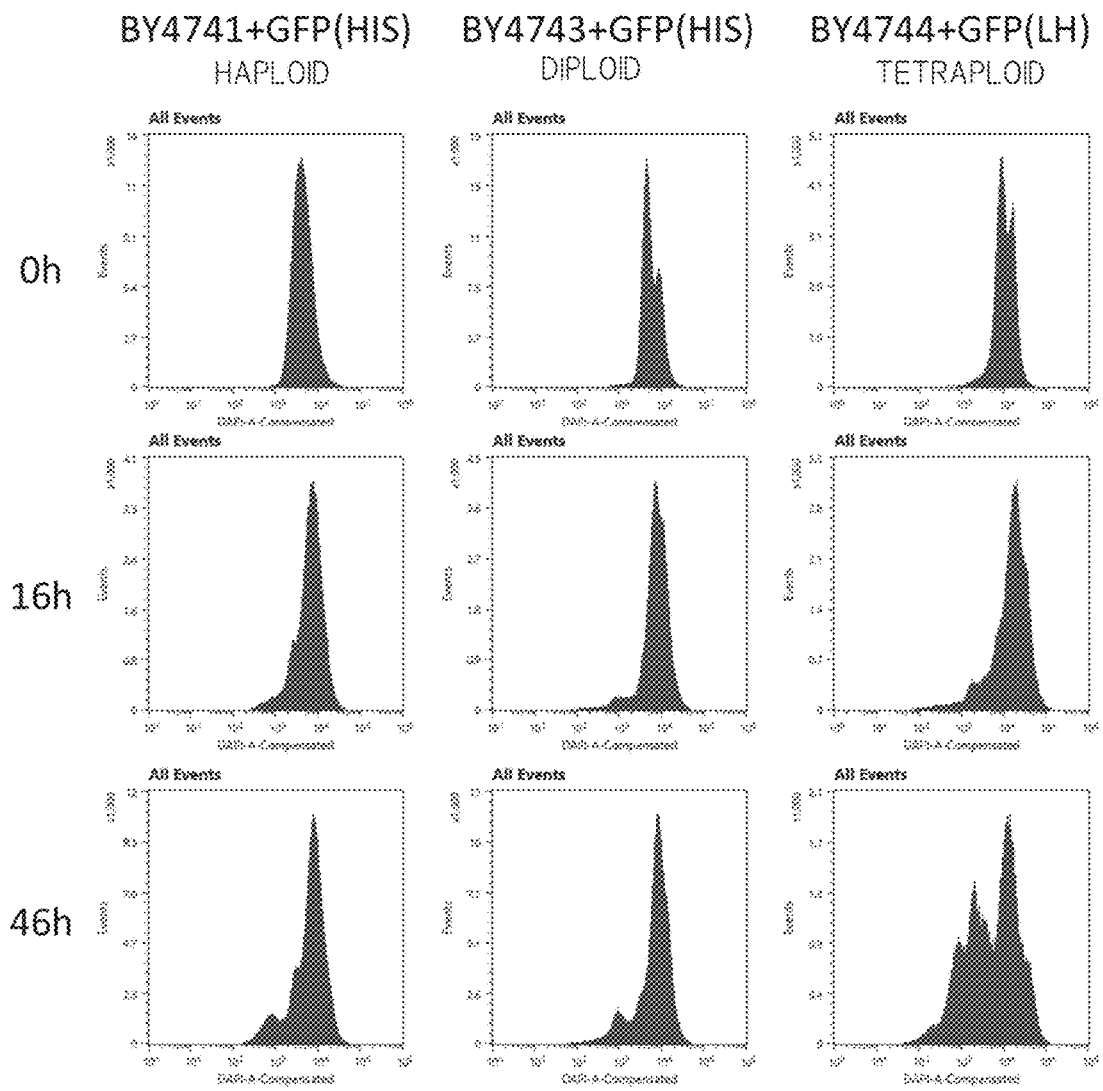
FIG. 17 shows ploidy histograms by TaqI treatment time using haploid, diploid and tetraploid yeasts.

TaqI expression was induced at 35° C. in each doubled yeast as TaqI was mildly activated as in the Sixteenth Example. After 0, 16 and 46 hours the yeasts were collected and fixed with 70% ethanol, and genome DNA was fluorescent stained with DAPI dye. A nuclear phase analysis was performed by flow cytometry using the fluorescent stained doubled yeasts. The results are shown in FIG. 17. As shown in FIG. 17, there was an increase in the frequency of individuals with increased or decreased ploidy in the doubled yeasts.

Eighteenth Example (Evolutionary Breeding of Xylose Utilization Ability by Genome Doubling and Genome Rearrangement)

(Obtaining OC2-A Strain)

An OC2-A strain was prepared comprising a xylose utilization gene introduced into the wine yeast OC-2 strain. That is, based on the OC700 strain (Japanese Patent Application Laid-open No. 2014-193152) comprising a xylose utilization gene introduced into the wine yeast OC-2 strain, the ADH2 gene was destroyed while the ADH1 gene was amplified to obtain an OC2-A strain with an introduced mhpF gene (from E. coli).

(Obtaining OC2-A(CF) Strain)

Using the OC2-A strain, evolutionary breeding of xylose utilization ability was accomplished as follows by genome rearrangement. An OC2-A(K1URA3) strain comprising a URA3 gene from Kluyveromyces lactis and an OC2-A (KmTRP1) strain comprising the TRP1 gene from Kluyveromyces marxianus introduced into the OC2-A strain were prepared. Cell fusion was performed with the two strains by the protoplast-PEG method, to prepare a cell fused strain OC2-A(CF).

An OC2-A(CF)+TaqI strain was obtained by transforming the OC2-A(CF) strain with the TaqI gene yeast expression vector pORF-pGAL1-TtTaqIopt-tDIT1(AUR). Using the OC2-A(CF)+TaqI strain, the medium was replaced with YPG+0.5 mg/L AbA medium as in the Twelfth Example, and the yeast was cultured overnight at 20° C. to induce TaqI expression. TaqI activation was then performed for 8 to 24 hours at 35° C., and samples that had undergone recovery culture with YPD medium+0.5 mg/L AbA medium were taken as a genome rearrangement yeast library.

(Obtaining OC2A-C5 Strain)

Figure 18:
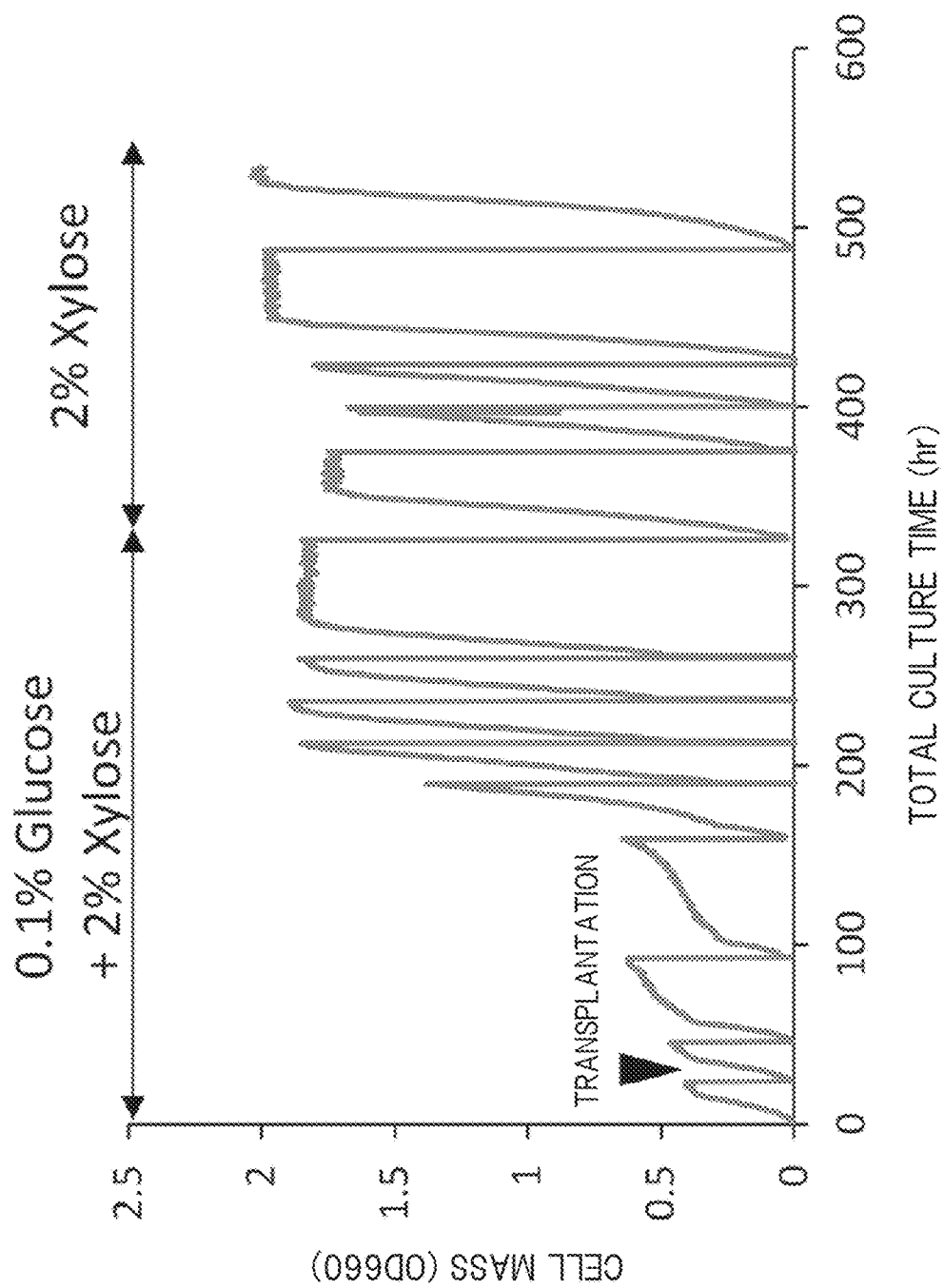
FIG. 18 shows changes in cell mass in an integration culture step.

This was cultured in medium having xylose as the principal sugar source, and integration culture was carried out by repeated transplanting at 35° C. After the start of integration culture, the yeast was cultured up to about 300 hours in YPX medium to which a small amount of glucose had been added (10 g/L Yeast extract, 20 g/L Peptone, 1 g/L Glucose, 20 g/L Xylose). The medium was then changed to YPX medium having only xylose as the sugar source (10 g/L Yeast extract, 20 g/L Peptone, 20 g/L Xylose), and integration culture was performed for about 200 hours. Changes in cell mass during these culture steps are shown in FIG. 18. The culture liquid after integration culture was streaked on YPD agar plates, and a single strain was taken as the OC2A-C5 strain.

(Xylose Utilization Ability Test of OC2A-C5 Strain)

The xylose utilization ability of the OC2A-C5 strain was evaluated by a fermentation test. The OC2-A strain, OC2-A(CF) strain and OC2A-C5 strain were each seeded to OD600=1.0 on 5% xylose fermentation medium (10 g/L Yeast extract, 50 g/L Xylose), and a fermentation test was performed at 32° C. Sampling was performed at 0, 16, 24, 48 and 72 hours, and xylose and ethanol were measured by HPLC. The results are shown in FIG. 19.

Figure 19:
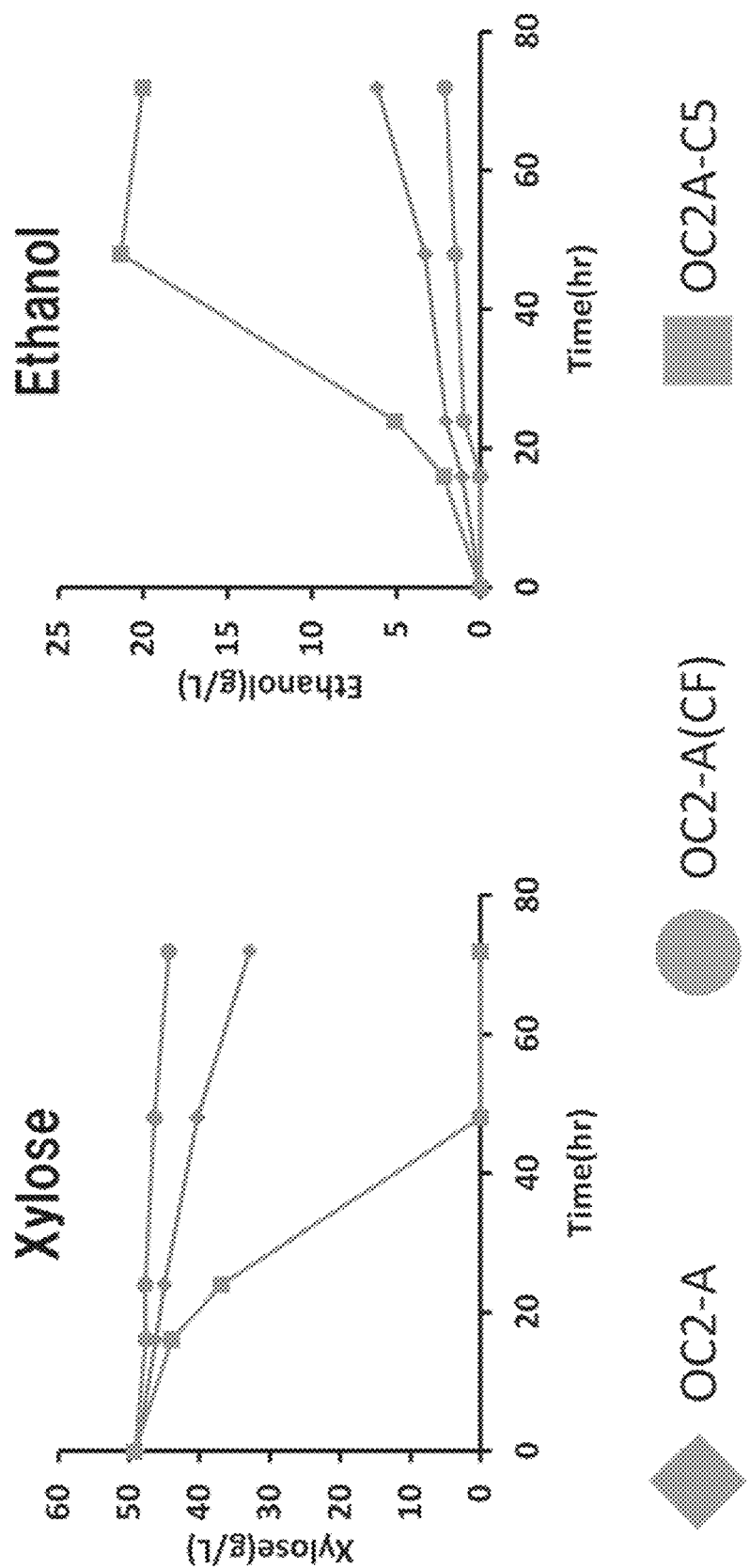
FIG. 19 shows the results of a fermentation test of the xylose utilization ability of the OC2A-C5 strain (5% xylose fermentation medium)

As shown in FIG. 19, the OC2A-C5 strain had much greater xylose utilization ability than either the parent OC2-A strain or the cell fused OC2-A(CF) strain, and by 48 hours the 50 g/L of xylose had been completed consumed, producing 21.3 g/L of ethanol.

Fermentation ability was also evaluated as in the utilization ability test above using a glucose+xylose mixed fermentation medium with a high sugar concentration (10 g/L Yeast extract, 80 g/L Glucose, 100 g/L Xylose). The results are shown in FIG. 20.

Figure 20:
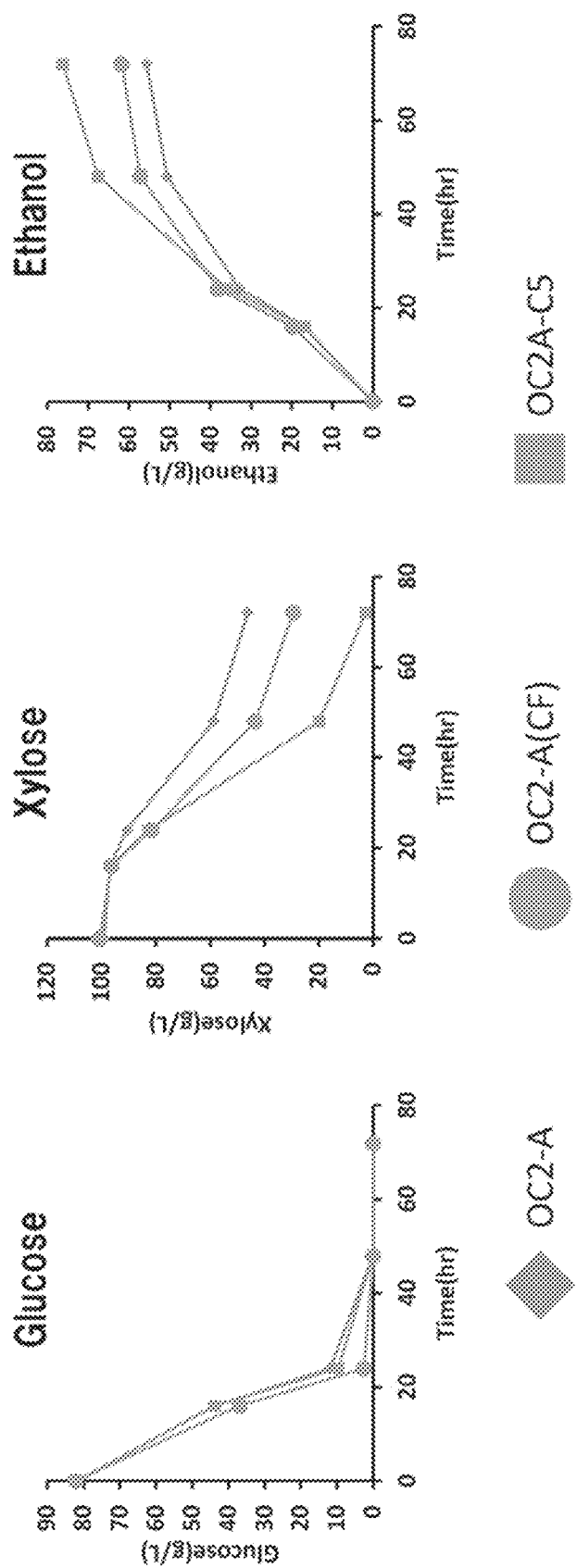
FIG. 20 shows the results of a fermentation test of the xylose utilization ability of the OC2A-C5 strain (high sugar concentration glucose+xylose mixed fermentation medium, 80 g/L glucose and 100 g/L xylose)

As shown in FIG. 20, the OC2A-C5 strain exhibited greater xylose utilization ability than the parent OC2-A strain or the cell fused OC2-A(CF) strain, and by 72 hours the 80 g/L of glucose and 100 g/L of xylose had been completely consumed, producing 76.2 g/L of ethanol.

As shown in FIGS. 19 and 20, the OC2A-C5 strain had dramatically increased xylose utilization ability, and also greater ability to produce ethanol and the like by fermentation. In particular, about 1.3 times the fermentation ability of the OC2-A(CF) strain and about 1.4 times the fermentation ability of the OC2-A strain were achieved even in a fermentation test using a realistic fermentation condition (high sugar concentration), indicating an excellent practical xylose utilization ability.

These results show that a useful OC2A-C5 strain could be obtained by expressing and activating the TaqI gene in the OC2-A(CF)+TaqI strain having the introduced TaqI gene, and performing integration culture under the evolutionary pressure of xylose-containing medium to cause evolutionary change and selection. That is, cells in which a double-stranded DNA breakage enzyme has been expressed and activated can be proliferated under any conditions to thereby efficiently obtain cells suited to those conditions.

Nineteenth Example (Evolutionary Breeding of Heat Resistance by Genome Rearrangement)

TaqI treatment was performed as in the Eighteenth Example using the OC2A-C5 strain prepared in the Eighteenth Example, to prepare a genome rearrangement yeast library. This was then cultured at 39° C. to 41° C. in YPX medium (10 g/L Yeast extract, 20 g/L Peptone, 20 g/L Xylose), and integration culture by repeated transplanting was performed for about 500 hours. The culture liquid after integration culture was streaked on YPD agar plates, and a single strain was taken as the OC2A-TT strain.

Heat resistance was evaluated by a fermentation test at 40° C. with this OC2A-TT strain. The OC2-A strain, OC2-A(CF) strain, OC2A-C5 strain and OC2A-TT strain were each seeded to OD600=1.0 on glucose+xylose mixed fermentation medium (10 g/L Yeast extract, 30 g/L Glucose, 30 g/L Xylose), and a fermentation test was performed at 40° C. Sampling was performed at 0, 16, 24, 48 and 65 hours, and glucose, xylose and ethanol were measured by HPLC. The results are shown in FIG. 21.

Figure 21:
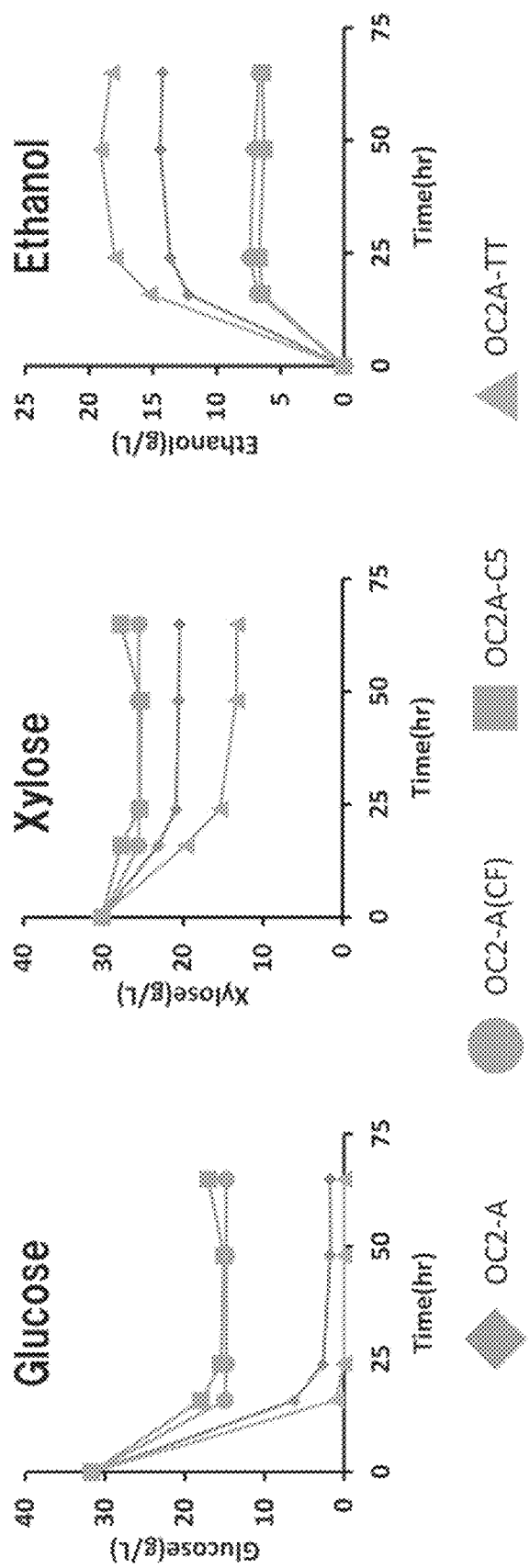
FIG. 21 shows the results of a fermentation test of the heat resistance (40° C.) of the OC2A-TT strain (glucose+xylose mixed fermentation medium, 30 g/L glucose and 30 g/L xylose).

As shown in FIG. 21, The OC2A-TT strain had increased proliferation ability (heat resistance) at 40° C. in comparison with the other strains. As shown in FIG. 21, the heat resistance of the OC2A-TT strain was dramatically higher, it exhibited good xylose utilization ability even in high-temperature culture, and the ability to produce ethanol and the like by fermentation was also increased due to the dramatic increase in xylose utilization ability. In particular, about 1.2 times the fermentation ability of the OC2-A strain and about 3 times the fermentation ability of the OC2-A(CF) strain and OC2A-C5 strain was achieved even in a fermentation test using a realistic fermentation condition (high sugar concentration), indicating excellent practical utility in terms of heat-resistance in particular.

These results show that the useful strain OC2A-TT could be obtained by expressing and activating the TaqI gene in the OC2-A(CF)+TaqI strain having the introduced TaqI gene, and performing integration culture under the evolutionary pressure of high temperature to cause evolutionary change and selection. That is, cells in which a double-stranded DNA breakage enzyme has been expressed and activated can be proliferated under any conditions to thereby efficiently obtain cells suited to those conditions.

CITATION LIST

Patent Literature 1: Japanese Patent Application Laid-open No. 2011-160798
Patent Literature 2: Japanese Patent Application Laid-open No. 2006-141322
Patent Literature 3: Japanese Patent Application Laid-open No. 2012-44883
Patent Literature 4: Japanese Patent Application Laid-open No. H11-151050
Non Patent Literature 1: Nature. 2010 Nov. 11; 468(7321): 321-5
Non Patent Literature 2: Plant Cell. 2007 Oct. 19(10): 3090-9
Non Patent Literature 3: PLoS Biol. 2008 Jul. 15; 6(7): e174
Non Patent Literature 4: Nature. 2006 Oct. 5; 443(7111): 541-7
Non Patent Literature 5: Cell. 2013 Jan. 31; 152(3): 394-405

The invention claimed is:

1. A method comprising:
performing an artificial genome increasing operation on a first eukaryote to form a second eukaryote, wherein one or more cells of the second eukaryote is a polyploid having a genome set that is tetraploid or higher ploidy, which is maintained through mitosis, and has a ploidy greater than the inherent ploidy of the first eukaryote,
transforming the one or more cells of the second eukaryote with an expression vector capable of expressing a gene coding for a protein having double-stranded DNA breakage activity or supplying a protein having double-stranded DNA breakage activity to the one or more cells of the second eukaryote,
either after the one or more cells of the second eukaryote have been transformed with the expression vector and the protein having double-stranded DNA breakage activity has been expressed in the one or more cells of the second eukaryote, or after the protein having double-stranded DNA breakage activity has been supplied to the one or more cells of the second eukaryote, modifying the genome set of the second eukaryote by causing the protein to act within the one or more cells of the second eukaryote, and
after causing the protein to act within the one or more cells of the second eukaryote, inactivating the double-stranded DNA breakage activity of the protein, wherein the first eukaryote is:
a non-mammal animal or a cell derived from a non-human animal,
a plant,
a yeast, or
a koji mold, and
the protein is a frequent restriction enzyme having a 4-base or 5-base recognition site.

2. The method according to claim 1, wherein the modification of the genome set of the second eukaryote is one or more genetic recombination selected from the group consisting of genetic mutation by substitution, insertion or deletion of one or more bases, chromosome inversion, unequal crossover, crossover, translocation, duplication and deletion, copy number decrease, copy number increase, chromosome polyploidization and chromosome aneuploidization.

3. The induction method according to claim 1, wherein the modification of the genome set of the second eukaryote is a genetic recombination that includes chromosome aneuploidization.

4. The induction method according to claim 1, wherein the modification of the genome set of the second eukaryote is a genetic recombination that includes a genome size decrease or increase.

5. The induction method according to claim 1, wherein the modification of the genome set of the second eukaryote is a genetic recombination that includes deletion or duplication of part of a chromosome.

6. The induction method according to claim 1, wherein the frequent restriction enzyme is derived from a thermophilic bacterium and has an optimum temperature for double-stranded DNA breakage activity in a temperature range of from 50° C. to 80° C.

7. The induction method according to claim 6, wherein the modifying is carried out at a temperature lower than the optimum temperature for the double-stranded DNA breakage activity of the protein.

8. The induction method according to claim 1, wherein the frequent restriction enzyme used to modify the genome set is expressed within the one or more cells of the second eukaryote that have been transformed with the expression vector.

9. The induction method according to claim 1, wherein the frequent restriction enzyme is a restriction enzyme derived from a thermophilic bacterium.

10. The induction method according to claim 9, wherein the frequent restriction enzyme is TaqI.

11. The induction method according to claim 1, wherein the first eukaryote is the plant, the yeast, or the koji mold, and
the artificial genome increasing operation uses a doubling inducing agent.

12. The induction method according to claim 1, wherein the first eukaryote is the cell derived from the non-human animal, the yeast, or the koji mold, and
the artificial genome increasing operation uses cell fusion.

13. A method comprising:
performing an artificial genome increasing operation on a first eukaryote to form a second eukaryote, wherein one or more cells of the second eukaryote is a polyploid having a genome set that is tetraploid or higher ploidy, which is maintained through mitosis, and has a ploidy greater than the inherent ploidy of the first eukaryote, transforming the one or more cells of the second eukaryote with an expression vector capable of expressing a gene coding for a protein having double-stranded DNA breakage activity or supplying a protein having double-stranded DNA breakage activity to the one or more cells of the second eukaryote, either after the one or more cells of the second eukaryote have been transformed with the expression vector and the protein having double-stranded DNA breakage activity has been expressed in the one or more cells of the second eukaryote, or after the protein having double-stranded DNA breakage activity has been supplied to the one or more cells of the second eukaryote, modifying the genome set of the second eukaryote by causing the protein to act within the one or more cells of the second eukaryote, and after causing the protein to act within the one or more cells of the second eukaryote, inactivating the double-stranded DNA breakage activity of the protein and obtaining a population of modified eukaryotes, wherein the first eukaryote is:
- a cell derived from a non-human animal,
- a plant,
- a yeast, or
- a koji mold, and the protein is a frequent restriction enzyme having a 4-base or 5-base recognition site.

14. The production method according to claim 13, further comprising selecting a target eukaryote based on any indicator from the population of modified eukaryotes and subjecting the target eukaryote to a further modification step.

15. A method comprising:
performing an artificial genome increasing operation on a first eukaryote to form a second eukaryote, wherein one or more cells of the second eukaryote is a polyploid having a genome set that is tetraploid or higher ploidy, which is maintained through mitosis, and has a ploidy greater than the inherent ploidy of the first eukaryote, transforming the one or more cells of the second eukaryote with an expression vector capable of expressing a gene coding for a protein having double-stranded DNA breakage activity, after the one or more cells of the second eukaryote have been transformed with the expression vector and the protein having double-stranded DNA breakage activity has been expressed in the one or more cells of the second eukaryote, modifying the genome set of the second eukaryote by causing the protein to act within the one or more cells of the second eukaryote such that a eukaryote population carrying a modified genome set is obtained, and after causing the protein to act within the one or more cells of the second eukaryote, inactivating the double-stranded DNA breakage activity of the protein, wherein the first eukaryote is:
- a cell derived from a non-mammal animal,
- a plant,
- a yeast, or
- a koji mold, and the protein is a frequent restriction enzyme having a 4-base or 5-base recognition site.

16. The induction method according to claim 1, wherein the first eukaryote is a cell derived from the non-human animal.

17. The induction method according to claim 16, wherein the non-mammal animal is a fish.

18. The induction method according to claim 1, wherein the first eukaryote is the yeast.

19. The induction method according to claim 1, wherein the first eukaryote is the koji mold.

* * * * *